US011173324B2

(12) United States Patent
Paysan et al.

(10) Patent No.: US 11,173,324 B2
(45) Date of Patent: Nov. 16, 2021

(54) ITERATIVE IMAGE RECONSTRUCTION IN IMAGE-GUIDED RADIATION THERAPY

(71) Applicants: Varian Medical Systems, Inc., Palo Alto, CA (US); Varian Medical Systems International AG, Steinhausen (CH)

(72) Inventors: Pascal Paysan, Basel (CH); Marcus Brehm, Zürich (CH); Adam Wang, Palo Alto, CA (US); Dieter Seghers, Zürich (CH); Josh Star-Lack, Palo Alto, CA (US)

(73) Assignees: VARIAN MEDICAL SYSTEMS, INC., Palo Alto, CA (US); VARIAN MEDICAL SYSTEMS INTERNATIONAL AG

( * ) Notice: Subject to any disclaimer, the term of this patent is extended or adjusted under 35 U.S.C. 154(b) by 621 days.

(21) Appl. No.: 15/952,996

(22) Filed: Apr. 13, 2018

(65) Prior Publication Data
US 2018/0229056 A1 Aug. 16, 2018

Related U.S. Application Data

(63) Continuation of application No. PCT/US2016/056539, filed on Oct. 12, 2016.
(Continued)

(51) Int. Cl.
*A61N 5/10* (2006.01)
*G06T 11/00* (2006.01)
(Continued)

(52) U.S. Cl.
CPC ............ *A61N 5/1039* (2013.01); *A61B 6/032* (2013.01); *A61B 6/4085* (2013.01);
(Continued)

(58) Field of Classification Search
CPC .......................... A61B 6/302; G06T 2211/424
See application file for complete search history.

(56) References Cited

U.S. PATENT DOCUMENTS 6,421,411 B1 7/2002 Hsieh et al.
2007/0242867 A1 10/2007 Jan et al.
(Continued)

FOREIGN PATENT DOCUMENTS

CN  101449979 A  6/2009
CN  102918565 A  2/2013
(Continued)

OTHER PUBLICATIONS

European Application No. EP16856068.8, "Partial Supplementary European Search Report", dated May 10, 2019, 16 pages.
(Continued)

*Primary Examiner* — Angela M Hoffa
*Assistant Examiner* — Younhee Choi
(74) *Attorney, Agent, or Firm* — Su IP Consulting

(57) ABSTRACT

Reconstruction of projection images of a CBCT scan is performed by generating simulated projection data, comparing the simulated projection data to the projection images of the CBCT scan, determining a residual volume based on the comparison, and using the residual volume to determine an accurate reconstructed volume. The reconstructed volume can be used to segment a tumor (and potentially one or more organs) and align the tumor to a planning volume (e.g., from a CT scan) to identify changes, such as shape of the tumor and proximity of the tumor to an organ. These changes can be used to update a radiation therapy procedure, such as by altering a radiation treatment plan and fine-tuning a patient position.

15 Claims, 12 Drawing Sheets

Related U.S. Application Data

(60) Provisional application No. 62/242,967, filed on Oct. 16, 2015.

(51) Int. Cl.
   *A61B 6/03* (2006.01)
   *A61B 6/00* (2006.01)

(52) U.S. Cl.
   CPC .......... *A61B 6/4441* (2013.01); *A61B 6/5205* (2013.01); *A61N 5/1045* (2013.01); *A61N 5/1081* (2013.01); *G06T 11/006* (2013.01); *G06T 11/008* (2013.01); *G06T 2211/424* (2013.01)

(56) References Cited

U.S. PATENT DOCUMENTS

| | | | |
|---|---|---|---|
| 2010/0246751 A1 | 9/2010 | Bruder et al. | |
| 2010/0278413 A1 | 11/2010 | Jarisch | |
| 2012/0308099 A1* | 12/2012 | Benson | G06T 11/006 382/131 |
| 2012/0328173 A1* | 12/2012 | Sachs | A61B 6/503 382/131 |
| 2013/0188856 A1* | 7/2013 | Adler, Jr. | A61N 5/107 382/132 |
| 2015/0103968 A1 | 4/2015 | Jin et al. | |
| 2015/0131774 A1 | 5/2015 | Maurer, Jr. et al. | |
| 2015/0221124 A1 | 8/2015 | Noo et al. | |
| 2016/0015350 A1* | 1/2016 | Chang | G06T 11/003 250/362 |
| 2016/0073994 A1* | 3/2016 | Fujisawa | G06T 7/0016 382/131 |
| 2017/0100088 A1* | 4/2017 | Simon | A61B 6/4085 |

FOREIGN PATENT DOCUMENTS

| | | |
|---|---|---|
| CN | 103052959 A | 4/2013 |
| CN | 103961128 A | 8/2014 |
| CN | 104821002 A | 8/2015 |
| JP | 10075947 | 3/1998 |
| KR | 1020130055510 | 5/2013 |
| WO | 2017066248 | 4/2017 |

OTHER PUBLICATIONS

Wei et al., "Using GPUs to Learn Effective Parameter Settings for GPU-Accelerated Iterative CT Reconstruction Algorithms", GPU Computing Gems Emerald Edition, Applications of GPU Computing Series, Jan. 1, 2011, pp. 693-708.

Erdogan et al., "Ordered Subsets Algorithms for Transmission Tomography", Physics in Medicine & Biology, vol. 44, 1999, pp. 2835-2851.

Feldkamp et al., "Practical Cone-Beam Algorithm", Journal of the Optical Society of America A, vol. 1, Issue 6, 1984, pp. 612-619.

Feldmar et al., "Rigid, Affine and Locally Affine Registration of Free-Form Surfaces", Hal Archives-Ouvertes, Inria, Mar. 1994, pp. 1-40.

Gordon et al., "Algebraic Reconstruction Techniques (ART) for Three-Dimensional Electron Microscopy and X-Ray Photography", Journal of Theoretical Biology, vol. 29, Issue 3, Dec. 1970, pp. 477-481.

Pham et al., "Introduction of Online Adaptive Radiotherapy for Bladder Cancer Through a Multicentre Clinical Trial (TransTasman Radiation Oncology Group 10.01): Lessons Learned", Journal of Medical Physics, vol. 38, No. 2, Apr.-Jun. 2013, pp. 59-66.

Pluim et al., "Mutual Information Based Registration of Medical Images: A Survey", IEEE Transactions on Medical Imaging, vol. 22, Issue 8, Aug. 2003, pp. 1-21.

Shepp et al., "Maximum Likelihood Reconstruction for Emission Tomography", IEEE Transactions on Medical Imaging, vol. MI-1, No. 2, Oct. 1982, pp. 113-122.

Veiga et al., "Toward Adaptive Radiotherapy for Head and Neck Patients: Feasibility Study on Using CT-to-CBCT Deformable Registration for "Dose of the Day" Calculations", Medical Physics, vol. 41, Issue 3, Mar. 2014, pp. 031703-1-031703-12.

Wang et al., "Accelerated Statistical Reconstruction for C-Arm Cone-Beam CT Using Nesterov's Method", Medical Physics, vol. 42, Issue 5, May 2015, pp. 2699-2708.

Yang et al., "Evaluation of On-Board kV Cone Beam CT (CBCT)-Based Dose Calculation", Physics in Medicine & Biology, vol. 52, 2007, pp. 685-705.

PCT/US2016/056539, "International Search Report and Written Opinion", dated Jan. 23, 2017, 14 pages.

PCT/US2016/056539, "International Preliminary Report on Patentability", dated Apr. 26, 2018, 10 pages.

\* cited by examiner

ITERATIVE IMAGE RECONSTRUCTION IN IMAGE-GUIDED RADIATION THERAPY

CROSS-REFERENCES TO RELATED APPLICATIONS

The present application is a continuation of International Application No. PCT/US2016/056539, filed Oct. 12, 2016, which claims benefit and priority under 35 U.S.C. § 119(e) to U.S. Provisional Application No. 62/242,967, filed Oct. 16, 2015, the entire contents of which are herein incorporated by reference for all purposes.

BACKGROUND

In radiation therapy, a treatment plan is first determined. The patient is typically imaged using computed tomography (CT), and the resulting data is used to determine a treatment plan of one or more treatment sessions, potentially over multiple days. It is important to have the patient in a specific position during treatment that matches the position in which the planning CT was taken. But, the CT machine is different than the radiation treatment machine, and thus there are difficulties in obtaining accurate matching positions. To address this problem, some techniques perform image-guided radiation therapy (IGRT), where the radiation treatment machine includes an imaging apparatus.

In IGRT, projection-based matching and volume-based matching are typically used. For projection-based, two projection images can be acquired only with source angular position differing by 90 degree. Those two images can be matched to digital reconstructed radiographs (DRRs) of the planning CT (forward projection of planning CT). For volume-based matching, pre-treatment on-board cone-beam computed tomography (CBCT) imaging can be applied for daily patient positioning. A reconstruction of a volume can be performed based on the acquired projection images and then the volumes can be matched.

The CBCT can be used to move the patient into a position that corresponds to a position the patient was in for the diagnostic CT. A three-dimensional patient volume is typically determined using filtered back projection (FBP) [J. Opt. Soc. Am. 1984;A1:612-619]. An operator of the radiation treatment machine can manually move the patient by viewing images of the patient volume and comparing the rough outlines in the patient volume to the volume from the diagnostic CT.

Such volume-based position corrections using current CBCT techniques can sometimes account for only large errors in patient position through manual correction, but are otherwise limited due to lower image quality compared to diagnostic CTs. And sometimes, current CBCT techniques may fail to help in patient positioning when imaging soft tissue.

There are technical differences between both systems, such as the imaging detector, the resulting ability to reduce scatter and noise correlation, the cone angle, the rotation speed, and many more. All of the technical differences lead to worse soft tissue discrimination in the abdominal and pelvic regions for CBCT images. Consequently, patient positioning for these regions mainly relies on bony matches or on surrogates like markers/clips that must be implanted prior to the treatment. And, due to such limitations, patient positioning is still the exclusive main use case, and thus the use of imaging to guide radiation therapy has been limited.

BRIEF SUMMARY

Embodiments provide systems, methods, and apparatuses for improved image-guided radiation therapy. Reconstruction of projection images of a CBCT scan is performed by generating simulated projection data, comparing the simulated projection data to the projection images of the CBCT scan, determining a residual volume based on the comparison, and using the residual volume to determine an accurate reconstructed volume. The reconstructed volume can be used to segment a tumor (and potentially one or more organs) and align the tumor to a planning volume (e.g., from a CT scan) to identify changes, such as shape of the tumor and proximity of the tumor to an organ. These changes can be used to update a radiation therapy procedure, such as by altering a radiation treatment plan and fine-tuning a patient position.

Other embodiments are directed to systems and computer readable media associated with methods described herein.

A better understanding of the nature and advantages of embodiments of the present invention may be gained with reference to the following detailed description and the accompanying drawings.

DETAILED DESCRIPTION

Image quality of state of the art three-dimensional onboard imaging for radiation therapy is deteriorated by image noise and image artifacts. Current techniques for using data from CBCT scans provide limited benefit for tailoring radiation therapy to the most current CBCT scan. Embodiments address such image quality problems by applying improved reconstruction techniques. Such improved reconstruction can involve iterations of using a reconstructed volume to simulate two-dimensional projections, which can then be compared to the actual projections images of the CBCT scans. A residual volume can be determined based on the comparison and a new reconstructed volume can be determined.

With such image reconstruction methods the image quality is enhanced and thus the patient positioning ability is increased. Other embodiment can use such reconstructed volumes to perform on-line adaptive planning for the radiation treatment. Such improvements to reconstructed volumes increase image quality, especially in terms of soft tissue contrast, which can improve patient positioning abilities and adaptive planning for abdominal and pelvic regions.

A radiation treatment system is first described, and then aspects of imaging. A general workflow of image-guided radiation therapy is then described, followed by adaptive operation using reconstruction embodiment, and further details about reconstruction techniques.

I. Treatment System

Figure 1:
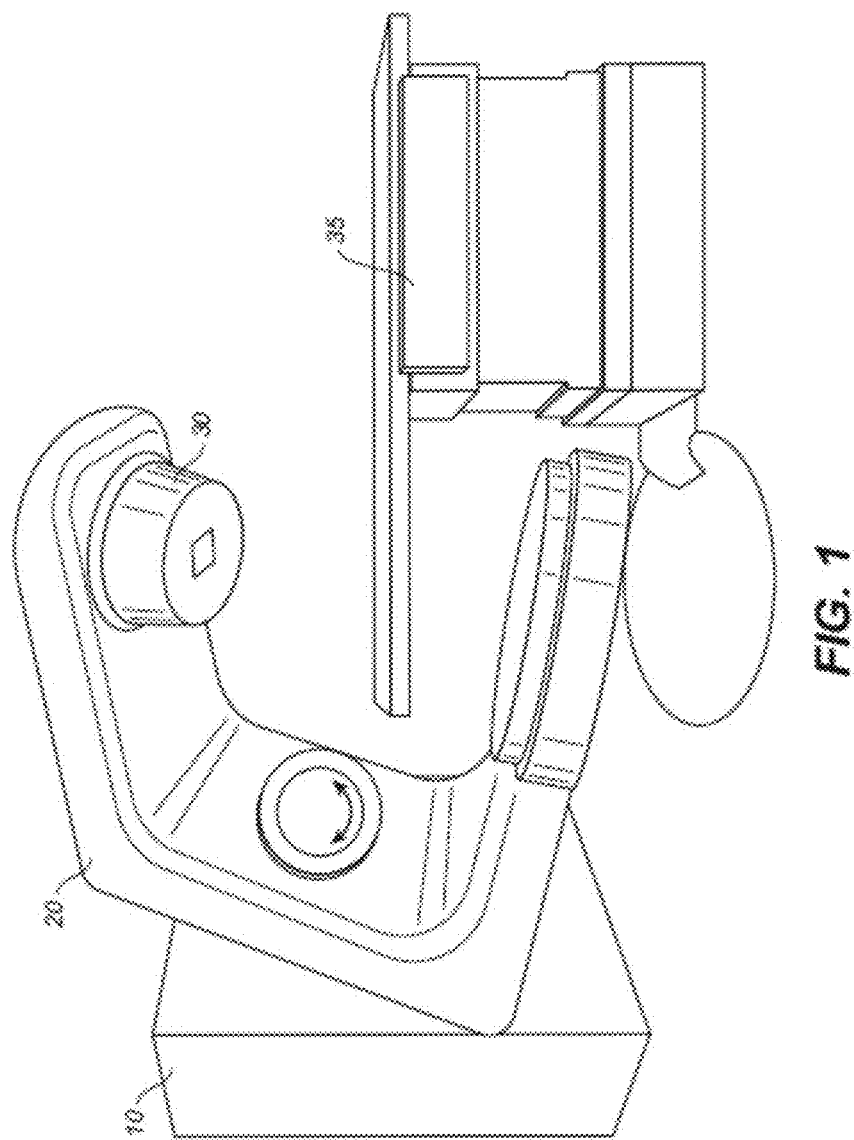
FIG. 1 is a perspective view of a radiation therapy system.
Figure 2:
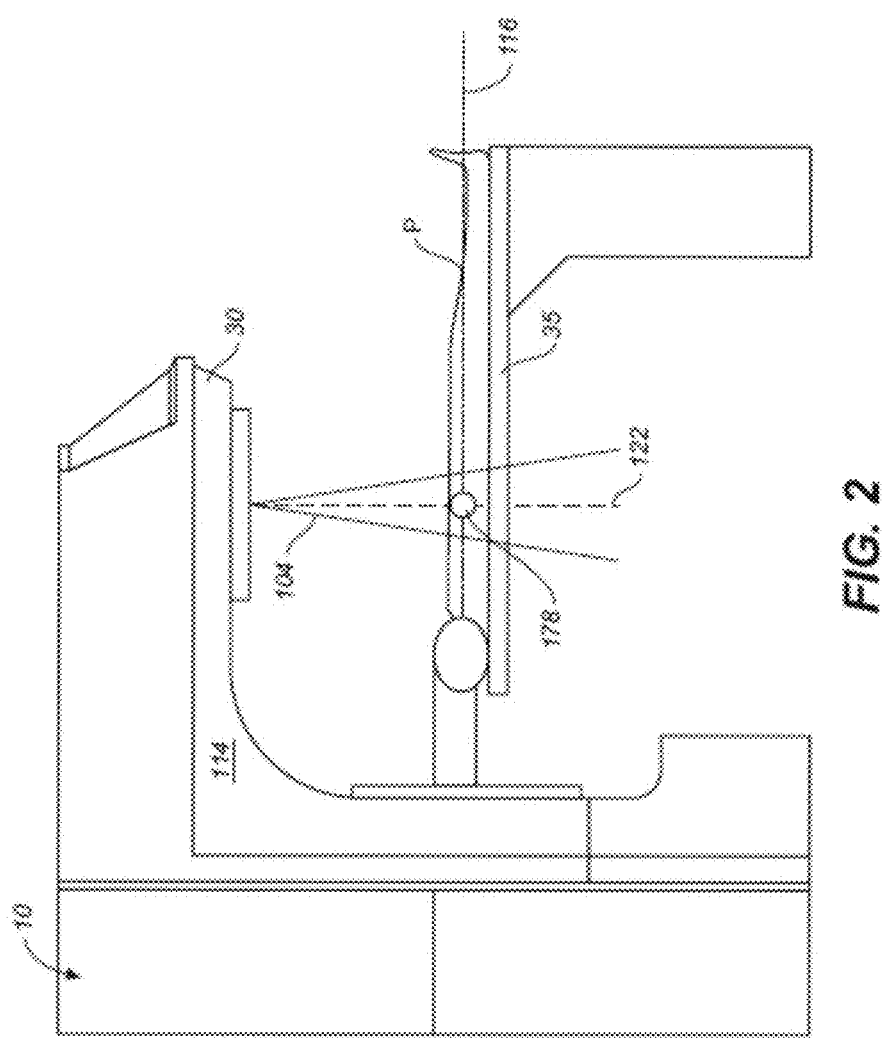
FIG. 2 is a side view of a radiation therapy system.

FIGS. 1 and 2 depict a radiation therapy system of the type which may be used in connection with the present invention. Referring to FIG. 1, a perspective view of radiation therapy system (in this case a linear accelerator) is shown. Typically, such a system is capable of generating either an electron (particle) beam or an x-ray (photon) beam for use in the radiotherapy treatment of patients on a treatment table 35. Other radiation therapy systems are capable of generating heavy ion particles, such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10, there is arranged a control unit (not shown), which includes operational electronics for controlling the different modes of operation of the accelerator. A high voltage source is provided within the stand or in the gantry, to supply voltage to an electron gun (not shown) positioned on an accelerator guide located in gantry 20. Electrons are emitted from the electron gun into the guide (not shown), where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation therapy system of the type that may be used in connection with the present invention is shown. A patient P is shown lying on treatment table 35. X-rays formed as described above are emitted from the target in treatment head 30 in a divergent beam 104. Prior to treatment, imaging of patient P may be performed using a similar divergent beam, also called a cone-beam.

Typically, a patient plane 116, which is perpendicular to the page in FIG. 2, is positioned about one meter from the x-ray source or target, and the axis of gantry 20 is located on patient plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 2) is positioned at the exit of head 30, to further shape the x-ray beam. Since its introduction in 1990, the MLC has become a standard feature of most radiation therapy systems. Current MLCs sold by the assignee of the present invention use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,"), as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head, and the MLC. In IMRT, the leaves of the MLC are moved, such that the treatment volume comprises the total volume exposed during the course of a treatment. In arc therapy, the gantry is moved while radiation is delivered.

Modern radiation therapy techniques involve the use of a treatment plan designed to irradiate a desired target volume, usually corresponding to a tumor, with a desired dose of x-rays (or other radiation). Most treatment planning involves the use of the MLC to provide conformal and/or intensity modulated irradiation. Generally speaking, a treatment plan comprises irradiating one or more selected portions of the treatment volume with a calculated dose of x-rays, and often involves irradiating a treatment area from a plurality of different angles where, in the case of arc therapy, the dose may be delivered while the gantry is rotated.

Various treatment planning software and other tools are available for developing specific treatment plans, and the details of the various techniques for creating such plans are known. After a treatment plan is created, it can be implemented, in part, by controlling the angle of incidence and the leaves of the MLC so as allow the desired radiation dose to reach the selected portions of the treatment volume from the selected angles or while the gantry is rotating. In the simplest type of treatment plan, the MLC is adjusted to provide static conformal irradiation of a specific site from a single angle. In more complex plans, the leaves are moved into different positions between or during irradiations. The leaves of the MLC can either be moved iteratively into different positions while the beam is off, with irradiation between movements (e.g., such that the leaves are static during x-ray emission), or they can be continually moved during irradiation in a "sliding window" or other variable aperture technique. As noted above, an important aspect of the conformal and IMRT techniques that are associated with the use of MLCs is the ability to provide a desired dose of radiation to a target volume while minimizing the dose delivered to adjacent healthy tissue.

Several techniques have been developed to create treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a treatment plan. Typically, such planning starts with volumetric information about the target tumor and about any nearby tissue structures, as may be determined from a diagnostic CT scan.

Such information may comprise a map of the planning target volume ("PTV"), such as a prostate tumor, which is prescribed by the physician to receive a certain therapeutic radiation dose with allowable tolerances. Volumetric information about nearby tissues may include, for example, maps of the patient's bladder, spinal cord, and rectum, each of which may be deemed an organ at risk that can only receive a much lower, maximum prescribed amount of radiation without risk of damage. This volumetric information along with the prescribed dose limits and similar objectives set by the medical professionals can be the basis for calculating an optimized dose distribution and the treatment plan to deliver it. The volumetric information may, for example, be reduced to an objective function or a single figure of merit that accounts for the relative importance of various trade-offs inherent in such a plan, along with constraints that must be met for the plan to be medically acceptable or physically possible.

Treatment planning algorithms can account for the capabilities of the specific radiation therapy system they are used with. For example, the type, energy level and fluence of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

II. Combined Imaging System

The radiation therapy system of FIGS. 1 and 2 may also perform imaging, e.g., cone-beam computed tomography (CBCT). Some general aspects of imaging are now described separate from the treatment aspects, but one will appreciate that a same machine may include both imaging and treatment aspects.

Figure 3:
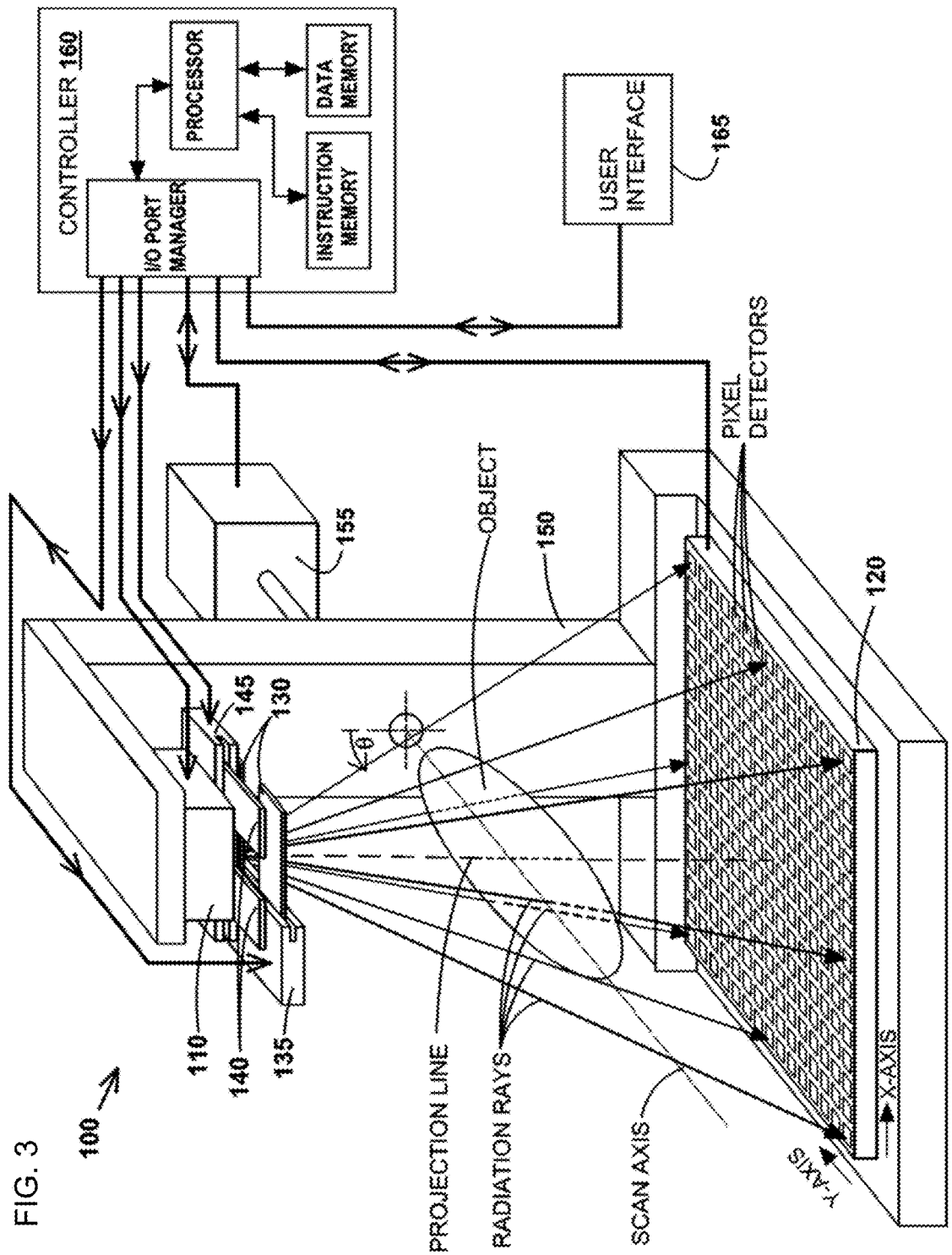
FIG. 3 is a schematic diagram of an exemplary imaging system according to the system inventions of the present application.

FIG. 3 is a schematic diagram of an exemplary imaging system 100 according to the system inventions of the present application. Various components of exemplary imaging system 100 may be optional, such as fan blades. System 100 comprises a radiation source 110, a two-dimensional imaging device 120 disposed opposite to radiation source 110 along a projection line, a first set of fan blades 130 disposed between the radiation source and the two-dimensional imaging device, a first fan-blade drive 135 that holds fan blades 130 and sets their positions. The edges of fan blades 130 are oriented substantially perpendicular to the scan axis (defined below), and are substantially parallel with the trans-axial dimension (defined below) of imaging device 120.

As an option, system 100 may further comprise a second set of fan blades 140 disposed between the radiation source and the two-dimensional imaging device, and a second fan-blade drive 145 that holds fan blades 140 and sets their positions. The edges of fan blades 140 are oriented substantially parallel with the scan axis (defined below), and are substantially perpendicular to the axial dimension (defined below) of imaging device 120. The fan blades are disposed closer to radiation source 110 than imaging device 120. The fan blades are normally kept wide open to enable the full extent of imaging device 120 to be exposed to radiation, but may be partially closed according to the image anchoring embodiments described near the end of this document. The dimensions of radiation source 110, imaging device 120, and fan blades 130 and 140 (and their drives) have been enlarged in the figure relative to the size of object for the purposes of illustrating these components.

System 100 can further comprise a gantry 150 that holds radiation source 110, imaging device 120, and fan-blade drives 135 and 145 in fixed or known spatial relationships to one another. A mechanical drive 155 rotates gantry 150 about an object disposed between radiation source 110 and imaging device 120, with the object being disposed between fan blades 130 and 140 on the one hand, and imaging device 120 on the other hand. The term gantry has a broad meaning, and covers all configurations of one or more structural members that can hold the above-identified components in fixed or known (but possibly movable) spatial relationships. For the sake of visual simplicity, a gantry housing, gantry support, and fan-blade support are not shown. Also not shown are a "bow tie" filter for radiation source 110 and a support table for the patient (i.e., an object support member).

In some embodiments, gantry 150 of FIG. 3 can correspond to gantry 20 of FIG. 1, e.g., when radiation source 110 and imaging device 120 are mounted on a gantry of a treatment machine. Different radiation sources can be used for imaging and for treatment, or a same radiation source can be used. In other embodiments, imaging device 120 and radiation source 110 can be part of a separate machine from the treatment machine, e.g., not mounted on a gantry of a treatment machine.

Additionally, system 100 further comprises a controller 160 and a user interface 165, with controller 160 being electrically coupled to radiation source 110, mechanical drive 155, fan-blade drives 135 and 145, imaging device 120, and user interface 165. User interface 165 provides a human interface to controller 160 that enables the user to at least initiate a scan of the patient, and to collect measured projection data from the imaging device. User interface 165 may be configured to present graphic representations of the measured data.

In imaging system 100, gantry 150 is rotated about the patient during a scan, such that radiation source 110, fan blades 130 and 140, fan-blade drives 135 and 145, and two-dimensional imaging device 120 circle around the object. More specifically, gantry 150 rotates these components about a scan axis, as shown in the figure, where the scan axis intersects the projection line, and is typically perpendicular to the projection line. The patient is aligned in a substantially fixed relationship to the scan axis. The construction provides a relative rotation between the projection line on the one hand and the scan axis and an object aligned thereto on the other hand, with the relative rotation being measured by an angular displacement value θ. Mechanical drive 155 is mechanically coupled to gantry 150 to provide rotation upon command by controller 160.

The two-dimensional imaging device comprises a two-dimensional array of pixels that are periodically read to obtain the data of the radiographic projections. Imaging device 120 has an X-axis and a Y-axis, which are perpendicular to each other. Imaging device 120 is oriented such that its Y-axis is parallel to the scan axis. For this reason, the Y-axis is also referred to as the axial dimension of imaging device 120, and the X-axis is referred to as the trans-axial dimension, or lateral dimension, of device 120. The X-axis is perpendicular to a plane defined by the scan axis and the projection line, and the Y-axis is parallel to this same plane. Each pixel is assigned a discrete X-coordinate ("X") along the X-axis, and a discrete Y-coordinate ("Y") along the Y-axis. In typical implementations, the size of the array is 1024 pixels by 768 pixels, measuring approximately 40 cm by 30 cm, with the longer dimension of the array being oriented parallel to the X-axis. As used herein, the discrete X-coordinates start at −Xpix/2 and end at Xpix/2 (e.g., Xpix=1024), and the discrete Y-coordinates start at −Ypix/2 and end at Ypix/2 (e.g., Ypix=768). A smaller number of pixels are shown in the figure for the sake of visual clarity. The imaging device may be centered on the projection line to enable full-fan imaging of the object, may be offset from the projection line to enable half-fan imaging of the object, or may be movable with respect to the projection line to allow both full-fan and half-fan imaging of objects. As an example of a half-fan configuration, the imaging device may be offset from the center by 16 centimeters in its X-dimension when the imaging device has a span in the X dimension of 40 centimeters.

When controller 160 receives a request from the user to begin a scan of a patient, controller 160 instructs fan-blade drives 135 and 145 to set the fan blades 130 and 140, respectively, in open positions (or in partially closed positions as described in greater detail below for some embodiments), instructs mechanical drive 155 to begin a scan rotation of gantry 150, and instructs radiation source 110 to begin emitting radiation. As it rotates, mechanical drive 155 provides controller 160 with an indication of the angular displacement value θ. Controller 160 uses this information to read the values of imaging device 120's pixel detectors at selected angular displacement values θ to obtain the data for the radiographic projections. Typically, there are between 250 and 1000 projections taken in the 360-degree scan rotation (although less than 360-degree rotation can be performed), with each projection being spaced from adjacent projections by a set increment Δθ of angular displacement. The controller stores the data from each projection in a memory storage device, along with the angular displacement value θ at which the projection was taken. Scatter correction methods may be used to correct each projection for scattered radiation caused by scattering in the patient and the top cover of imaging device 120. Scattering can also be corrected for other elements, such as a treatment table, immobilization devices, antenna, and the like.

Controller 160 comprises a processor, an instruction memory for storing instruction sets that direct the operation of the processor, a data memory that stores pixel and other data values used by the present inventions implemented by the imaging system, and an I/O port manager that provides input/output data exchange between the processor and each of radiation source 110, mechanical drive 155, fan-blade drives 135 and 145, and imaging device 120. The instruction memory and data memory are coupled to the main processor through a first bidirectional bus, and may be implemented as different sections of the same memory device. Because of the large amount of data provided by the two-dimensional imaging device, the I/O port manager is preferably coupled to the main processor through a second bidirectional bus. However, the I/O port manager may be coupled to the main processor by way of the first bidirectional bus. The operation of the processor is guided by a group of instruction sets stored in the instruction memory, which is an exemplary form of computer-readable medium. Some of these instruction sets may direct the processor to generate estimates of scattered radiation in one or more of the projections. Additional instruction sets may direct the processor to correct the projections according to scatter-correction methods disclosed by the present application, or may direct the processor to store the raw projection data to a computer-readable medium, from which it may be exported to another processor that performs the correction.

III. Image Guided Radiation Therapy (IGRT)

After a CT scan, the patient volume can be computed for the fixed position the patient was in at the time of the CT scan. This patient volume is used to determine a treatment plan for the patient. As part of determining the treatment plan, it is generally assumed the patient is still and that the tumor generally does not change. Breathing and peristaltic motion may change tumor position and may have to be accounted for by planning target volume (PTV) margins, motion compensation, breath-hold, or gating techniques. For prostate cancer, several treatments can be determined for different rectum or bladder filling.

When it comes time for treatment, there are going to be some differences between the real patient and the computer model. The idea is to acquire images of the patient so that the patient's position and their posture can be adjusted, so that the patient very closely matches what was planned. With such a match, the actual treatment (e.g., the radiation dose distribution) that that patient gets will match to what was planned during the planning process.

A. General Workflow

Figure 4:
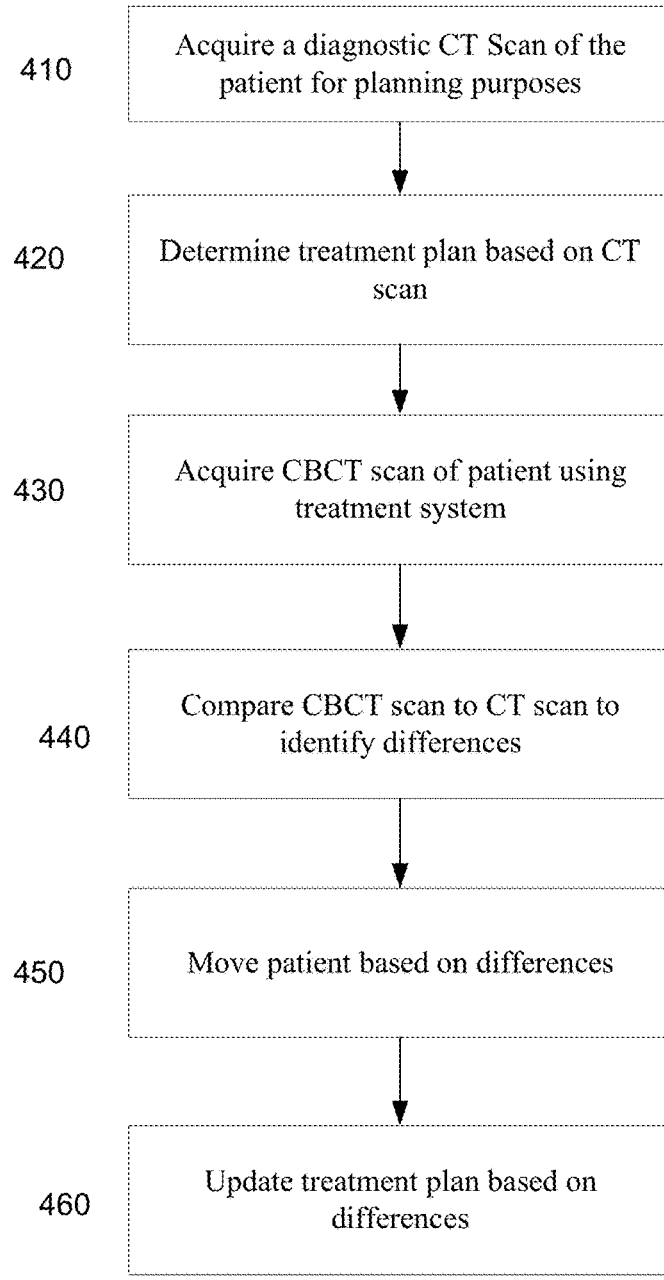
FIG. 4 is a flowchart of a method 400 for image guided radiation therapy according to embodiments of the present invention.

FIG. 4 is a flowchart of a method 400 for image guided radiation therapy according to embodiments of the present invention. Method 400 may be performed entirely or partially by the treatment machine, which can include a computer system.

At block 410, a diagnostic CT scan of the patient is acquired for planning purposes. The diagnostic CT machine is a dedicated machine (i.e., it does not also provide radiation treatment). The CT scan is used to create a virtual representation of the patient, or at least a virtual representation of a region of the patient. The region includes a tumor to which radiation is to be applied. In a diagnostic CT, cross-sectional imaging is performed. In the virtual representation, the patient is represented by several of those slices that form a volume, i.e. each voxel represents a small cubic region of the patient.

In some embodiments, for the diagnostic CT, the acquisition trajectory is a helix, as opposed to a circle or part of a circle, which is common for a CBCT scan. Typically, the radiation source and detector rotate around the imaging axis, and the patient table is moved simultaneously in parallel to the imaging axis. The detector is typically curved, instead of being flat, as is typical for CBCT. In some system, two source-detector-pairs exist in the machine.

At block 420, a treatment plan is determined based on the CT scan. The virtual representation can be used to determine an optimal treatment plan, e.g., to reduce risk healthy organs and optimize radiation received by the tumor. The optimization can vary multiple parameters, such as an MLC, trajectory of the radiation source, dosage at any time during a treatment session, number of treatment sessions, etc.

At block 430, a CBCT scan of patient is acquired using a radiation therapy system. The radiation therapy system may be of the type shown in any one of FIGS. 1-3. In the CBCT scan, the data are projective images, i.e. each pixel represents a line integral through the patient. As a single shot those data are also known as x-ray image. The CBCT scan would also be of a region of the patient that includes the tumor, and can include one or more organs.

At block 440, the CBCT scan is compared to the CT scan. More precisely, a reconstructed volume from the projected images of the CBCT scan can be compared to a planning volume the virtual representation from the CT scan. Certain embodiments describe volume-based matching in more detail below. For example, a reconstruction of a volume can be performed based on the acquired projection images and then the volumes can be matched. The comparison can identify differences between the reconstructed volume and the planning volume.

At block 450, the patient can be moved based on differences. For example, the reconstructed volume can be subjected to translations and rotations to align the anatomy in the reconstructed volume with the anatomy of the planning volume. The translations and rotations to achieve the alignment can correspond to the differences. The translations and rotations can be used to correct the patient positioning. For example, a treatment table (e.g., 35 in FIG. 2) can be moved automatically by a motor, where the movements correspond to the determined translations and rotations. If the alignment is already within a specified tolerance, then the patient can be kept in the current position that the CBCT scan was taken. As another example, the treatment system can output (e.g., by display or audio) changes to an operator, who can implement the changes.

At block 460, the treatment plan can be updated based on the differences. The updates to the treatment plan can vary and can include steps that are used to determine the original treatment plan. For example, the shape and/or size of the tumor may have changed. Thus, the dosage of radiation may need to be updated for a current treatment session and/or future treatment sessions. As another example, the proximity of the tumor to other organs may have changed. The trajectory of the radiation beam can be changed to accommodate the relative change in positions, so as to reduce the amount of radiation provided to the organs compared to what the current treatment plan would have provided.

B. Comparison of Images

Not all reconstruction techniques using data from a CBCT scan are sufficiently accurate for IGRT, as one can see from the images below. For example, current techniques applied in IGRT for reconstructing a volume from a CBCT scan provide a limited image quality that does not allow for the application of automatic segmentation and registration methods, and manual steps of alignment would take too long and/or not provide sufficient accuracy. Particular parts of the body can problematic, e.g., the pelvis region.

Figure 5A:
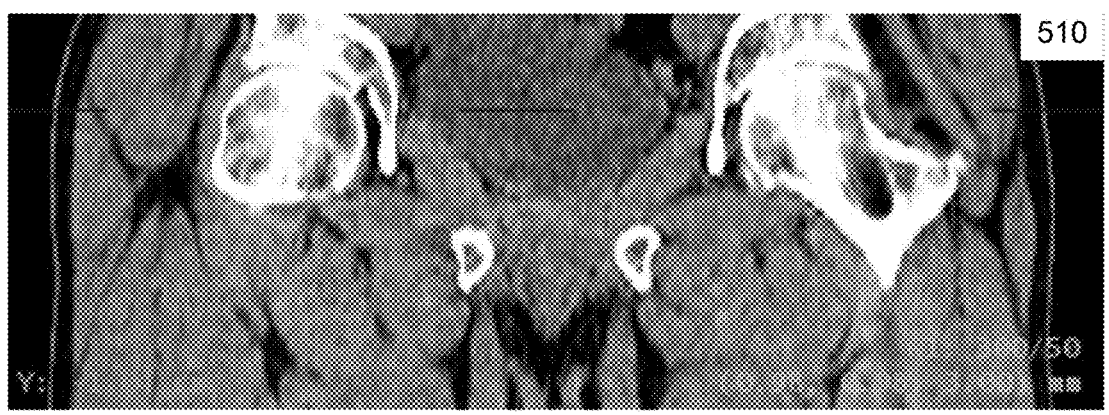
FIG. 5A shows a patient image from a planning CT scan that is used to determine a radiation treatment plan.

FIG. 5A shows a patient image 510 from a planning CT scan that is used to determine a radiation treatment plan. Such a planning patient image would not be a CBCT scan, but would be from a diagnostic CT machine. For a diagnostic CT machine, the source of radiation does expand in a cone-like fashion, but the cone is typically much smaller than for a CBCT scan. There are other difference between a CBCT machine and a CT machine, such as rotation speed, acquisition time, patient dose, noise level, soft tissue contrast, longitudinal coverage, and the like. Patient image 510 is for a prostate cancer patient.

Figure 5B:
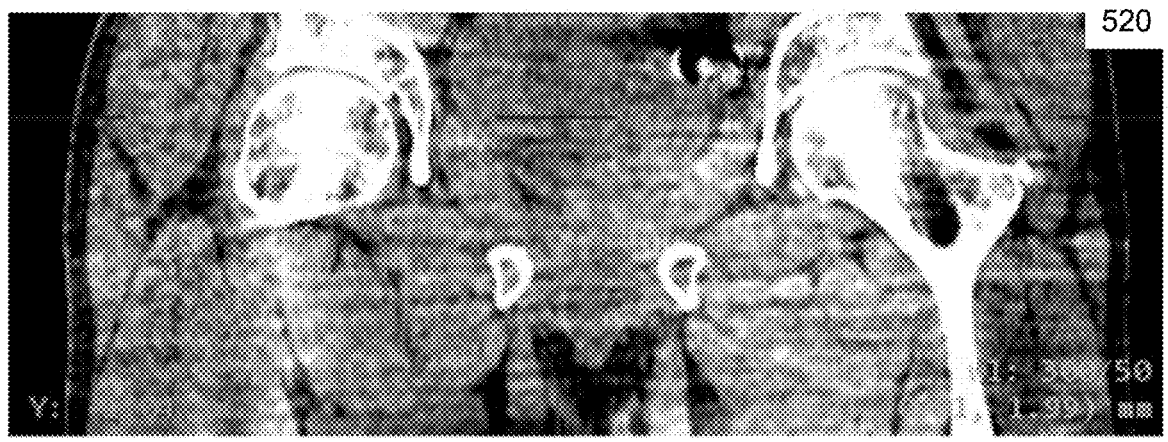
FIG. 5B shows a reconstructed image using filtered back projection (FBP).

FIG. 5B shows a reconstructed image 520 using filtered back projection (FBP). In IGRT the filtered back projection (FBP) [J. Opt. Soc. Am. 1984;A1:612-619] is state-of-the-art reconstruction method for three-dimensional onboard imaging. Reconstructed image 520 is a daily CBCT on True Beam machine. As can be seen, reconstructed image 520 is of much lower quality than patient image 510.

Figure 5C:
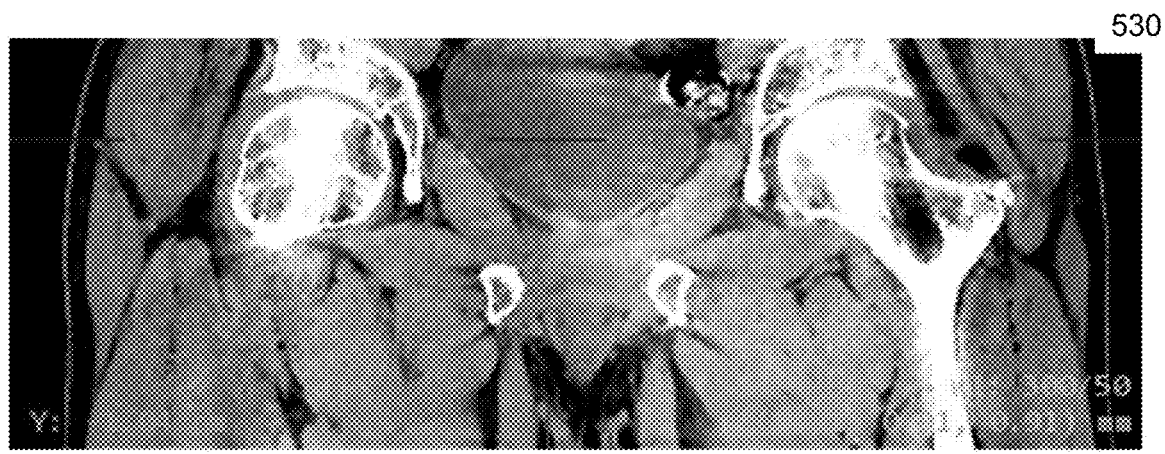
FIG. 5C shows an improved reconstructed image according to embodiments of the present invention.

FIG. 5C shows an improved reconstructed image 530 according to embodiments of the present invention. Image 530 is a re-reconstruction of True Beam dataset from FIG. 5B with an iterative reconstruction algorithm. Image 530 is more clear than image 520. Since the organs can be more clearly seen, this information can be used for more accurate positioning. Automatic segmentation and registration methods can be used, given the higher quality image.

IV. Reconstruction Algorithm

Some embodiments of the reconstruction algorithm include a pair of operators that operate between the two-dimensional projection data space and the three-dimensional volume data space. Below, these operators are called forward (3D into 2D) and backward (2D into 3D) projection operators. In some embodiments, an objective is to maximize the data fidelity that indicates how well a current reconstructed volume from the CBCT scan matches the measured projections. The reconstructed volume can be updated to increase the match, thereby obtaining a higher quality volume from the CBCT scan. An aim of some embodiments is to increase image quality without increasing imaging dose and by using the same imaging components as have been previously used. Other embodiments can decrease imaging dose without decreasing image quality.

In some embodiments, data fidelity is optimized by alternating an operation of the forward projector on the current reconstructed volume and an operation of a backward projector to determine the residual error compared to the measured projection data to compute the volume update. One implementation applies a mismatched operator pair of voxel-driven back projection and pixel-driven forward projection techniques. Both operators can be destination-driven, and thus not matched. Operators are called matched if one operator is the inverse operation of the other. For matching operators, one operator would be destination-driven and the other source-driven. Thus, if voxel-driven back projection and pixel-driven forward projection are destination driven, then the two operators do not match.

Both, forward and backward projection, can include a normalization step in order to, e.g., implicitly account for data redundancy and varying angular spacing. Data redundancy relates to information being measured more than once, as is typical. An example is to measure the same line integral just with exchanged source and detector pixel positions. Not all data is necessarily measured twice or more. The angular spacing regards source positions that belong to projection acquisitions.

A. Workflow

Figure 6:
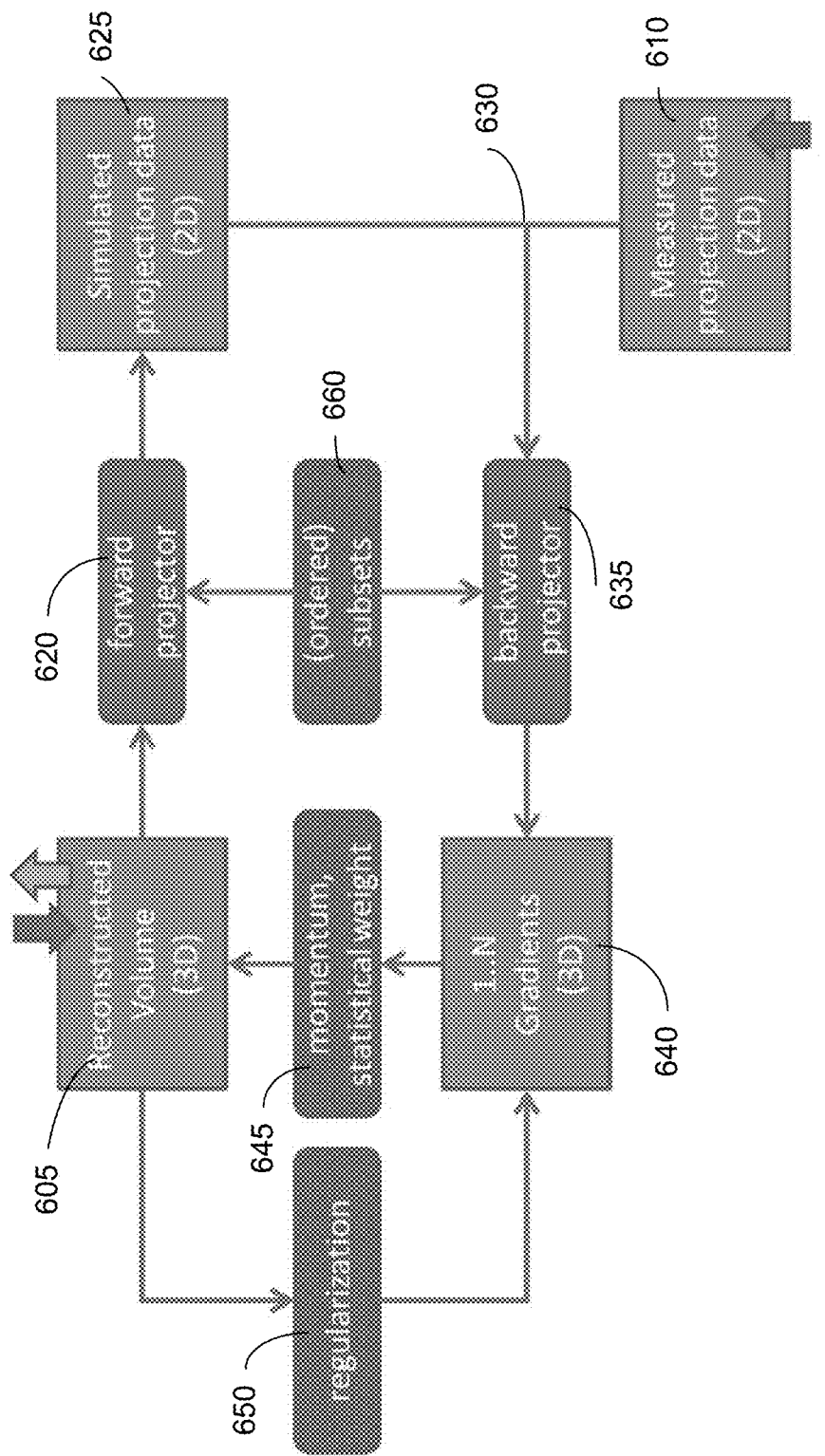
FIG. 6 shows the general workflow for iterative reconstruction according to embodiments of the present invention.

FIG. 6 shows the general workflow for iterative reconstruction according to embodiments of the present invention. Blocks with rounded corner are operations and others blocks represent data. Fields with brick wall background are optional elements, i.e. 645, 650, 660, and input arrow for 605. Red arrow represents input data and green arrow output data. The volumes can correspond to a region of a patient's body (e.g., a fixed length of the body or fixed body part, such as the head) or the entire patient's body.

The iterative reconstruction (IR) in FIG. 6 uses inputs of an initial reconstructed 3D volume 605 and measured 2D projection data 610. Each iteration can improve matching of the reconstructed 3D volume 605 to the measured 2D projection data 610. Forward projector 620 can generate simulated 2D projection data 625, which can be compared to measured 2D projection data 610 at node 630. The comparison can provide residual images that are used in backward projector to obtain a residual volume, also referred to as 3D gradients 640, which can be used in determining updated to reconstructed 3D volume 605. The iterations can be repeated until the gradients 640 become sufficiently small or a maximum number of iterations is reached, which may be one iteration.

1. Reconstructed Volume

The initial reconstructed volume can be a variety of volumes, e.g., an empty volume, a uniform volume (such as water or other liquid), a filtered back projection, and the like. For the uniform volume, reconstructed 3D volume 605 would have equal intensity everywhere. For example, the volume can be represented as an array of voxels in a grid. The uniform volume would have a same density in each voxel. An empty volume would correspond to a volume with all zeros in the voxels.

2. Forward Projector

Forward projector 620 simulates the results of an imaging of reconstructed volume 605, e.g., using simulated rays and scattering onto an image detector. The computer simulation can emit simulated x-rays from a radiation source, where a simulated x-ray interact with reconstructed volume 605 and are attenuated based on the trajectory of the x-ray. For a given position of the radiation source, the attenuated x-rays will reach an image detector that would detect a level of intensity that correspond to an amount of attenuation through reconstructed volume 605, resulting in one image of simulated projection data 625. The radiation source can be placed at a plurality of positions, with an image of simulated projection data 625 being determined for each position. The positions correspond to the positions of the actual radiation source used to create measured projection data 610. The plurality of positions correspond to different geometries of the radiation source relative to reconstructed volume 605 and the image detector.

As part of the simulation, the x-rays can be represented as photons that are transformed into electrical signals comparable to a digital camera. Forward projector 620 can simulate these processes of actual x-rays traveling through the actual volume and be detected by an actual image detector. The image detector has pixels, where a value of the pixel corresponds to all of the simulated x-rays that interact with pixel for a given position of the radiation source, thereby providing an image for that position. The pixel can effectively sum the intensities of the x-rays, and thus provide a measure of the attenuation from reconstructed volume 605. For example, the pixel value can equal the sum of the voxel value times the voxel dependent contribution for the voxels that the ray intersects.

3. Comparison with Measured 2D Data

Once simulated projection data 625 is obtained, a comparison can be made at node 630 to measured projection data 610 to determine an error between the two data sets. The error between the images of simulated projection data 625 and measured projection data 610 can be determined in a variety of ways. The error may be more than a simple arithmetic difference between each pixel of each corresponding image, the corresponding images are for a same geometry. For example, the error may include a conversion of the images to other spaces by logarithmic operations, and/or include optimization strategies based on penalty function like via Huber-loss-function. Logarithmic operations and Huber-loss-function can be defined by the data fidelity definition that is part of the optimization cost function.

The term residual refers to a broader class of errors existing between the two data sets. A residual image corresponds to the measured error between one image of simulated projection data 625 and measured projection data 610. As examples, the number of images for each data set can be about 600 or 700, with a corresponding number of residual images. Iterations using subsets (labeled as subsets 660) are discussed in detail below.

Ideally, the two data sets what exactly match, and thus reconstructed volume 605 would correspond to the actual volume of the patient. The amount of residual error in the residual images impacts backward projector 635. Generally, larger values in the residual images resultant larger gradients 640 for updating reconstructed volume 605.

There are different iterative reconstructions techniques available, e.g., algebraic reconstructions [J theor. Biol. 1970; 29(3):471-81] and statistical reconstructions [TMI 1982; 1(2):113-22.] depending on the chosen cost function and the respective optimization strategy. A log-likelihood cost function is used [Phys Med Biol. 1999; 44(11):2835-5] in certain implementations. The different techniques can affect how the gradient volume is created from the simulated and the measured projection data and how the statistical weighting is applied. Regardless of which technique is used, iterative procedures of data fidelity optimization described herein have a key advantage over FBP that is important for CBCT. Cone-beam artifacts increase with increasing cone angle, which can have a significant impact for CBCTs. Such artifacts are more emphasized in case of short scan (e.g., a 180 degree arc instead of 360 degree arc) due to redundancy weighting issues, which can depends on the projection image geometries. For example, if a 360° arc with centered detector is used, each voxel is measured twice for a certain angle direction. In most cases both measurements have different cone angles and thus the error due cone angles is averaged. In case of 180° plus fan angle arc, some voxel and angle directions are measured twice and some are measured just once. For the latter, the cone angle errors are not averaged, and thus are more prominent than for a 360 degree arc. These artifacts can be corrected for by the iterative manner of data fidelity optimization in IR methods described herein.

This use of iterative reconstruction can allow a variety of geometries. For example, the radiation source can rotate around the volume for 360° for a circular trajectory. But, other arcs can be used, and the trajectory of the radiation source during a simulated scan does not have to lie on an arc. In this manner, a number of different trajectories can be used, thereby allowing different trajectories to be used for generating measured projection data 610. Thus, the actual CBCT is not limited to a particular geometry. With FBP, the respective weighting must be derived analytically for each new trajectory type.

4. Backward Projector

Backward projector 635 can operate like an inverse of forward projector 620 in that race can be back traced from pixels of the residual images to determine contributions to voxels of the residual volume (also called gradients 640). The residual volume corresponds to the error in reconstructed volume 605 relative to the actual volume as measured by projection data 610. There are different techniques available for implementation of backward projector 635, e.g., source-driven or destination-driven.

For source-driven backward projection, an x-ray can be back traced from a pixel of the residual image through the volume to the radiation source, and voxels through which the x-ray pass can be identified. The contribution to a voxel can be determined as the product of a weight and the pixel value. The weight for a voxel (and thus the contribution) can be determined based on a voxel's distance to the x-ray (e.g., voxel center distance to the x-ray line) and/or the intersection length of the ray through the voxel.

For a destination-driven back projection, a destination voxel is selected and then projected onto the image detector, i.e. focal spot (source), voxel, and projected position are on a straight line. A value can be retrieved for this position from the projection image via interpolation, and the value is used to determine a contribution to the voxel for a given geometry of the radiation source and image detector.

Such analysis can be done for each residual image, with all the contributions from all the pixels of all the residual images being accumulated to determine attenuation values for each voxel of the residual volume. Accordingly, embodiments can sum over all the pixels representing the residual images, and add up their contributions to each voxel.

As mentioned above, for voxel-driven back projection, the position of a voxel projected on the detector is determined. This position might not correspond with the center of a pixel, but might be in between several pixels. In some implementations, the nearest pixel can be used. In other implementations, linear interpolation is applied as a mixture of neighboring pixel values depending on their distance to the projected position. Since the image detector is two-dimensional grid, the respective interpolation is bi-linear (projection image). Other interpolation techniques like cubic or B-spline are also possible.

The redundancy weighting within iterative reconstruction can be part of a normalization process consisting of one or two normalization steps. These steps can be performed as part of backward projector 635 and node 630. This normalization would depend on the projection image geometries.

5. Combination of Residual Volume and Previous Reconstructed Volume

The residual volume 640 can be applied to an update of reconstructed volume 605. As residual volume 640 is a measurement of the error between reconstructed volume 605 and the actual volume, reconstructed volume 605 can be updated to reduce the error. For example, if one started with uniform attenuation values for reconstructed volume 605, residual volume 640 can indicate different levels for increases and decreases of attenuation for certain voxels of residual volume 640.

Residual volume 640 can be used in a variety of ways to update reconstructed volume 605. For example, residual volume 640 can simply be added (with negative values for voxels corresponding to subtraction) to the previous reconstructed volume of the previous iteration. A scaling value can be multiplied to the values of residual volume 640 before the combination with the previous reconstructed volume. And, each voxel of residual volume 640 can have separate weightings.

In some implementations, previous residual volumes can be saved and used in a current update of reconstructed volume 605. Operator 645 can use these previous residual volumes as a momentum operator. The momentum operator can combine a current gradient with one or more previous gradients. Thus, a momentum can be formed from the history of previous gradients for each voxel, and that momentum can cause the update of each voxel to be impacted by momentum of changes in previous iterations for that voxel. In one implementation, a Newton-Raphson technique may be used to determine how the gradient values are to be used in the update, e.g., a mixing coefficient can be determined for each voxel of each previous residual volume.

In order to reduce the amount of storage, a linear combination of previous gradients can be stored, so that the memory usage does not increase for more iterations. For example, for the first iteration, there is only one gradient volume, which can be stored for the next iteration. For the second iteration, a linear combination of both gradient volumes is stored. For the third iteration, the third gradient volume is combined with the previous linear combination, and so on.

In some embodiments, statistical weights can be determined for each voxel, where the statistical weights affect the impact of the gradient for that voxel for an update. Operator 645 can use such statistical weights in performing the update. The statistical rates are described in more detail below. Weights dependent on projection image geometries can also be used.

At various parts of the workflow, a regularization process can be performed to reduce noise in reconstructed volume 605 and/or residual volume 640. Although regularization operator 650 is shown between reconstructed volume 605 and residual volume 640, regularization operator 650 can be performed at different sections of the process, and potentially multiple sections of the process. Regularization is described in more detail below.

B. Comparison

Figure 7B:
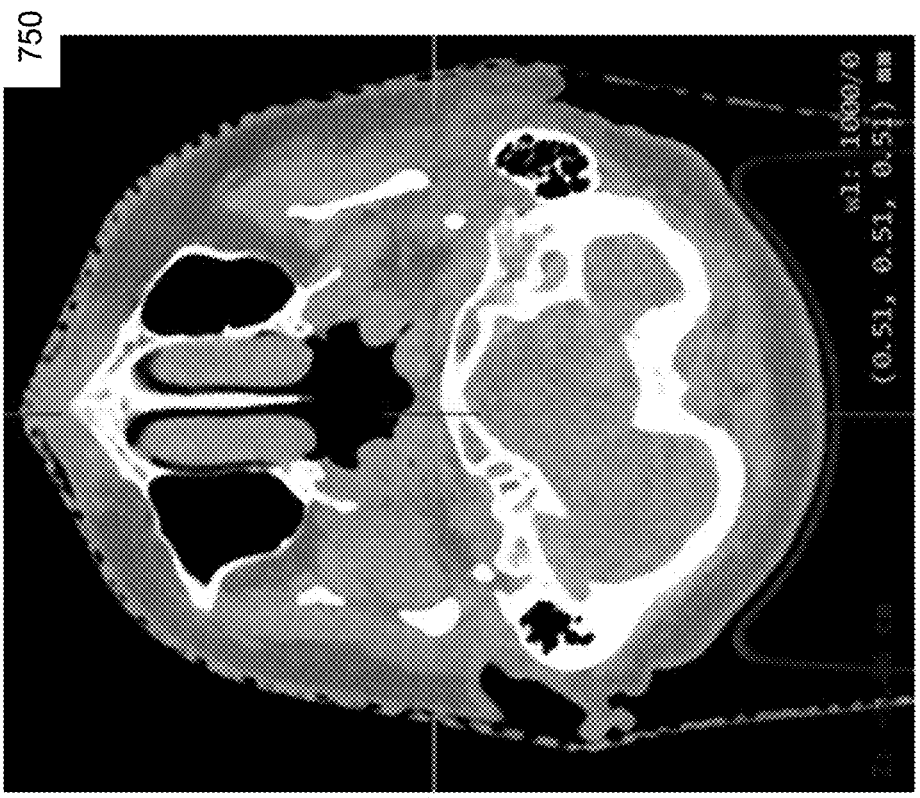
FIG. 7B shows a reconstructed image 750 with a reconstruction algorithm according to embodiments of the present invention.
Figure 7A:
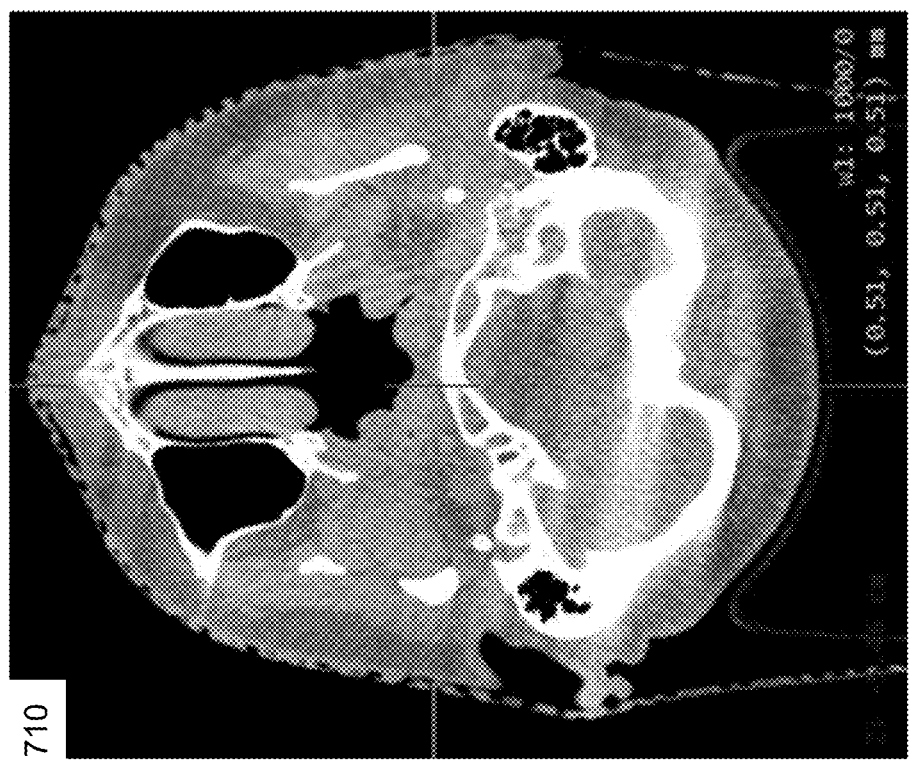
FIG. 7A shows a daily CBCT image 710 on a True Beam machine.

FIG. 7A shows a daily CBCT image 710 on a True Beam machine. Image 710 is a reconstructed CBCT image using FBP. Image 710 is of a head of the patient. A slice far from isocenter is shown here with cone beam artifacts present for the FBP case on the left. One can see substantial artifacts at the bottom of the image.

FIG. 7B shows a reconstructed image 750 with a reconstruction algorithm according to embodiments of the present invention. Reconstructed image 750 is substantially free of the artifacts from image 710. Additionally various features have higher contrast, and thus more definitive lines for alignment of the patient and updates to the treatment plan.

V. Adaptive Operation Using Iterative Reconstruction

Embodiments can provide higher quality images of a patient from a CBCT scan. The higher quality images can be used to adapt the operation of the treatment system. This adaptation can occur automatically, e.g., by moving a treatment table and/or updating the treatment plan.

A. Method

Figure 8:
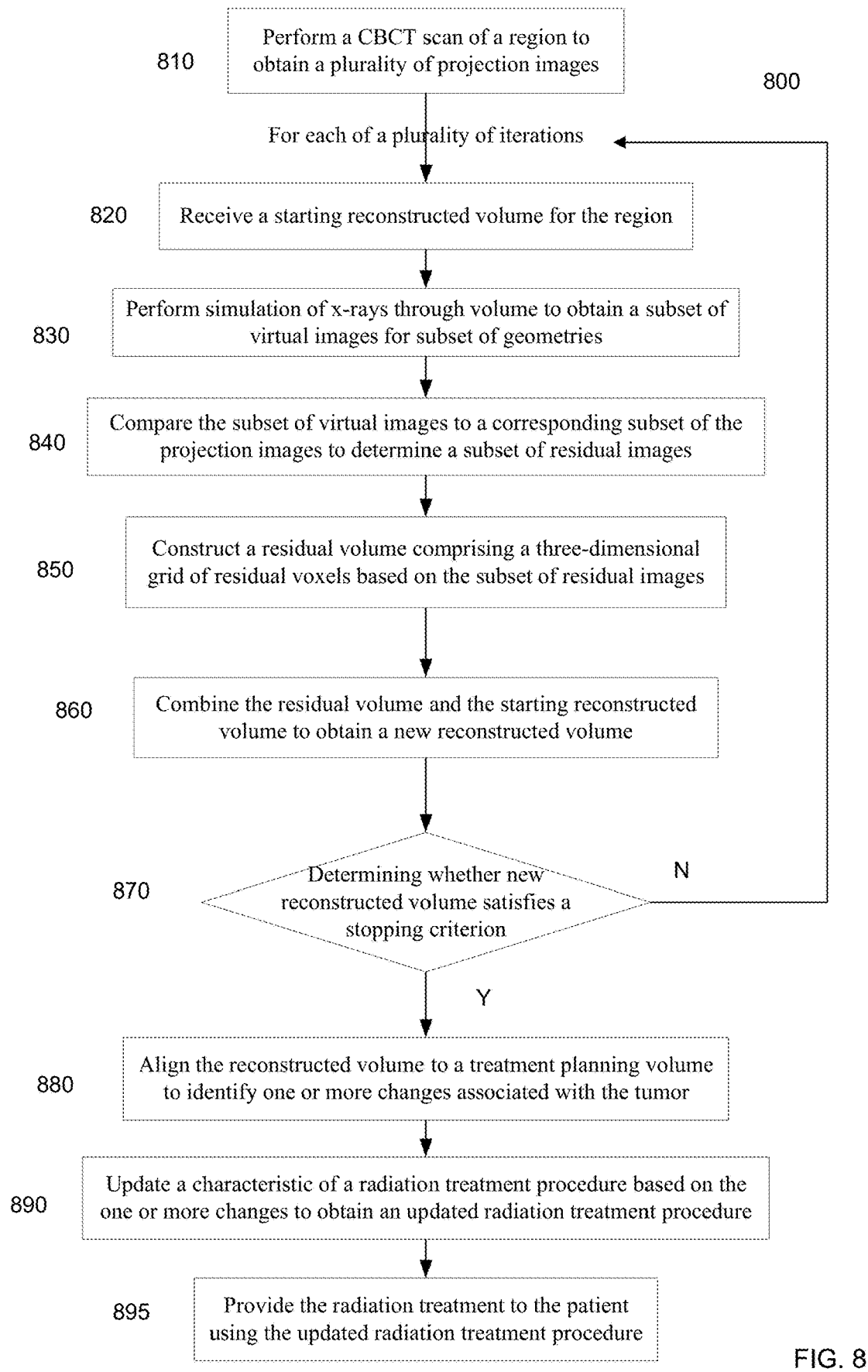
FIG. 8 is a flowchart of a method 800 for providing radiation treatment to a patient according to embodiments of the present invention.

FIG. 8 is a flowchart of a method 800 for providing radiation treatment to a patient according to embodiments of the present invention. The image reconstruction in method 600 can be performed by a computer system that part of or in communication with a radiation treatment system.

At block 810, a CBCT scan of a region of a patient is performed using a radiation source to obtain a plurality of projection images. Each projection image is taken at a different one of a plurality of geometries of the radiation source relative to the patient. The region of the patient includes a tumor. A CBCT image (e.g., image 530) is part of the reconstructed CBCT volume, while a projection image is a 2D image, e.g., of line integrals like an X-ray image.

Projection images may have different representations. For example, one representation is the intensity (counts) measured by the detector hardware. Another is the attenuation line integral value that is the negative logarithm of the measured intensities divided by the measured intensities without attenuating object in ray path. Any suitable representation may be used.

Blocks 820 to 870 can determine a reconstructed volume of the patient by performing one or more iterations of an iterative reconstruction. Each iteration can comprise blocks 820 to 870 and then repeat until a stopping criterion is met. A computer system is used to determine the reconstructed volume. The computer system can be part of an imaging device or a treatment system, e.g., part of any of the systems described in FIGS. 1-3.

At block 820, a starting reconstructed volume for the region is received. The starting reconstructed volume comprises a three-dimensional grid of voxels. The voxels can be of any shape, e.g., rectangular, triangular, hexagonal, etc. The starting reconstructed volume can be a default volume for the first iteration. Examples of a default volume are mentioned herein, such as a uniform volume.

At block 830, a simulation is performed to obtain a subset of virtual images for a subset of the geometries. For each of a subset of the plurality of geometries, rays can be simulated from the radiation source through the starting reconstructed volume to a virtual two-dimensional detector to obtain a subset of virtual images. The simulation can be performed as described for forward projector 620 of FIG. 6.

At block 840, the subset of virtual images are compared to a corresponding subset of the projection images to determine a subset of residual images. The subset of geometries can correspond to all of the geometries or just a portion, and the subset of virtual images would correspond to a same number of the projection images. Each residual image comprises an array of residual pixels. The comparison may be performed as described for node 630 of FIG. 6.

At block 850, a residual volume comprising a three-dimensional grid of residual voxels is constructed based on the subset of residual images. The residual volume can be constructed using a backward projector, e.g., backward projector 635 of FIG. 6. The residual volumes can correspond to gradients 640.

In some embodiments, constructing the residual volume can include determining residual voxels that rays intersect. For each of the residual pixels of each of the residual images, a set of residual voxels that intersect with rays from the residual pixel to the radiation source are determined. For each of the set of residual voxels, a contribution to the residual voxel can be determined. And, for each of the residual voxels, the contributions for the residual voxel can be accumulated (e.g., summed, potentially a weighted sum) to obtain the residual volume.

At block 860, the residual volume and the starting reconstructed volume are combined to obtain a new reconstructed volume. The two volumes can be combined in a variety of ways, as is described herein. For example, previous residual volumes can be used, e.g., as part of a momentum operation. Statistical weights can be used, and regularization can be applied.

In some embodiments, obtaining the new reconstructed volume includes a regularization term for providing a relatively smooth volume. For example, a penalty volume can be constructed that represents a variation of voxels of the starting reconstructed volume. The new reconstructed volume can be determined by combining the penalty volume, starting reconstructed volume, and the residual volume. In other embodiments, a smoothing function is applied to the residual voxels of the residual volume and/or to the new reconstructed volume as part of a regularization procedure.

In some implementations, combining the residual volume and the starting reconstructed volume includes weighting each residual voxel. For example, a respective weighting factor can be applied to each residual voxel of the residual volume. The weighting factor for a residual voxel can be determined based on a level of intensity corresponding to the projection images. For example, the statistical weights can depend on the intensities measured by the detector. The counts (intensities) can be low because only a low number of photons is emitted by the radiation source. The weighting factor for a residual voxel can also be determined based on a level of attenuation corresponding to the projection images, e.g., an attenuation value for the voxel, as determined from the projection images.

Multiple previous residual volumes can be used. In one implementation, one or more previous residual volumes from one or more previous iterations can be stored in memory. The one or more previous residual volumes can then be used in determining the new reconstructed volume. The one or more previous residual volumes can be stored separately or combined into a single previous residual volume, e.g., by adding the previous residual volumes together, potentially with different scaling factors for the different previous residual volume applied before summing.

At block 870, it is determined whether the new reconstructed volume satisfies one or more stopping criteria or whether another iteration is to be performed. An example of a stopping criterion include a specified number of iterations (e.g., 1, 5, 10, 20, etc.). With pre- and post-processing methods, embodiments may need only one iteration. Another example is the new reconstructed volume not being significantly different than the starting volume. A difference value between the two volumes can be measured and compared to a threshold. A specified number of consecutive iterations can be required to have a difference value that is less than the threshold.

At block 880, the reconstructed volume is aligned to a treatment planning volume to identify one or more changes associated with the tumor. A current radiation treatment plan had been determined using the treatment planning volume. The alignment can be performed as described herein. For example, pixels of the reconstructed volume can be superimposed onto the treatment planning volume such that a difference is minimized. The reconstructed volume can be shifted and rotated until a difference value is minimized. Deformable registration techniques can also be used, e.g., where the proximity of two voxels changes as part of the registration. This can be particularly useful when updating the treatment plan.

Example changes include size and shape of the tumor. Another example of a change is a position of the tumor relative to one or more organs, e.g., a proximity of the tumor to the one or more organs.

In some embodiments, segmentation can be performed before alignment. The segmentation can identify a particular organ (e.g., an at-risk organ near the tumor) or the tumor. The segmentation can identify segments in the volumes that correspond to a particular object, e.g., to the tumor or an organ. The alignment (also called registration) can align corresponding segments between the two volumes. In another embodiment, the verified segments can be transferred from the planning CT volume to the CBCT reconstructed volume by using deformable registration, instead of identifying the segments from just the CBCT reconstructed volume.

At block 890, a characteristic of a radiation treatment procedure is updated based on the one or more changes to obtain an updated radiation treatment procedure. Examples of a characteristic are described herein. For instance, the treatment plan can be updated, e.g., dosage of radiation can be changed, trajectory of the radiation beam can be changed, a shape of the radiation beam can be changed, or any multi-leaf collimator setting. The position of the patient can also be changed, e.g., by moving the treatment table with a motor or outputting new settings to be entered by an operator. Thus, the updated radiation treatment procedure can include updates to a patient position and/or updates to the treatment plan.

At block 895, the radiation treatment is provided to the patient using the updated radiation treatment procedure. For example, once the patient has been moved to a new position determined based on the reconstructed volume, the radiation beam can be applied. In some embodiments, the updated radiation treatment procedure may be for a future treatment session. In other embodiments, during treatment, further CBCT scans and reconstruction can be performed, and the radiation treatment procedure can be further updated during treatment.

The reconstruction can provide higher quality images probably sufficient for validity and re-planning purposes. Thus additional planning CTs acquired on a diagnostic CT device may not be needed. Often, additional planning CTs are used between treatment sessions to check validity or to update the treatment plan. With the higher quality images from the CBCT scans that are performed as part of a treatment sessions, the treatment plans can be updated just based on these higher quality images, and the additional CTs from diagnostic devices are not needed.

B. Patient Positioning

Side effects of radiation treatment depend highly on the sparing of healthy tissue and especially of organs at risk. Precise patient positioning is a key for successful treatment with high dose gradients and small safety margins. For certain cases, the bones are sufficient for positioning, but not for all. In other cases, the positions of tumor and organs at risk are required. This accounts in particular for the abdominal region where organs can change their position and/or their size (rectum, bladder, prostate, intestine, etc.). The CBCT images obtained from the reconstruction process can used for manual, semi-automatic, or automatic matching with the planning CT for patient positioning. As described above, the reconstructed volume can be matched to the training volume via an alignment process. The changes needed for alignment can be used to the patient into alignment.

For patient positioning, rigid registration algorithm can be utilized. Due to the lack of additional information like contours within CBCT images, such techniques are typically intensity or histogram-based only. Further details about registration methods based on mutual-information can be found in IEEE Trans Med Imaging. 2003 August; 22(8): 986-1004. By improving image quality, embodiments can provide automatic segmentation of tumor and organ contours. This additional information can improve local registration accuracy by using feature-based methods, e.g., as described in International Journal of Computer Vision, 18:99-119, 1996.

The positioning could be performed by an operator, as guided by the results of the registration process using the reconstructed volume. Such a change in the patient position made by the operator involves a change in a radiation treatment procedure. In other embodiments, differences from the reconstructed volume in the treatment volume can be used to shift the patient's treatment table. For example, the patient can be moved with a robotic couch inside the treatment room. Feedback can be used to move the patient so as to reduce the difference between the reconstructed volume in the planning volume. The positioning of the radiation source or other components of the treatment system can also be moved instead or in addition. Multiple CBCT scans can be used, with the reconstructed volume from each scan being used to determine any changes in patient position. Such ongoing adjustment can occur during treatment with a radiation beam.

C. Adaptive Planning

Treatment success also requires the treatment plan to be up-to-date. A treatment plan may be outdated due to different reasons, e.g. loss in weight, tumor shrinkage, variations in bladder and rectum volume, peristaltic motion, and many more. Accordingly, in addition to or instead of changes to the patient position, the treatment plan can also be adapted, e.g., via adaptive dose calculations at the time of the treatment session or during a treatment session. For example, there may be a problem that a tumor or organ has changed volume or has distorted because there are pressures that did not exist when the plan was created. Other example changes can include density and mass. To account for such changes, adaptive planning change the specific treatment, e.g., motion of radiation beam, intensity of the radiation beam at any given time, shape of the radiation beam, etc.

In some cases, the repositioning of patient can account for large errors, and changes to the treatment plan can adjust for remaining smaller errors. For example, changes to the relative positions of tumors and organs cannot be accounted for by simply moving the position of the patient. In some embodiments, a threshold difference between the reconstructed volume in the planning volume can be identified when to move the patient and/or change the treatment plan. Other embodiments can always perform such adjustments.

On-line adaptive planning means that the treatment plan adaption is based on the daily CBCT image obtained from the reconstruction process. Alternatively, a simulated CT based on the CBCT image can be applied, e.g., by matching the former planning CT. The contours from the initial planning CT may be transferred by applying (manual, semi-automatic, automatic) segmentation and registration tools, e.g. SmartSegmentation® and SmartAdapt® (Varian Medical Systems, Palo Alto, Calif.). A new treatment plan can be calculated using, e.g., Eclipse™ (Varian Medical Systems, Palo Alto, Calif.). Dose distributions already applied to the patient can be included based on the initial treatment plan or dose calculations based on the daily CBCTs. Off-line adaptive planning may also be used to update future treatment sessions.

The new treatment plan can be applied for the current treatment session or for the next treatment session. In various embodiments, two different types of workflow and time available for computation before results can be implemented. An application of the new plan within the same session is desirable for, e.g., hypo-fractioned treatments or in case of different bladder fillings. Here, massive computational power can be used to address the increased computational demand to be done within a short time frame. For others, like hyper-fractioned treatments, the new plan is applied for next session and more time (at least one day in general) is available to adapt the plan and less computationally powerful hardware may be sufficient. The improved image quality can be also valuable to choose the best from a set of already validated treatment plans.

To determine the updated treatment plan, some embodiments can start by changing the shape of the radiation beam as part of an optimization of the treatment plan. Other parameters can also be changed as part of the treatment plan optimization, such as the amount of dosage, the shaping of that dosage at a particular time, and the trajectory of the radiation source during treatment. Further details of techniques to update a treatment plan can be found in Med. Phys. 41 (3), March 2014.

VI. Computational Efficiency

The iterative process can be very computationally demanding compared to previous techniques, such as FBP, and can depend on the number of iterations required for reaching convergence criteria. Different embodiments can significantly reduce the number of iterations. In one approach, each subset of projections can be subjected to one iteration followed by an iteration for another subset. A single loop for one subset can be called a "subiteration" and the group of loops where each projection is processed exactly once can be considered an "iteration". Such processes can be enhanced by an optimal choice of projections grouped within a single subset called "ordered subsets" [Phys Med Biol. 1999; 44(11):2835-5]. Another option is to use momentum from previous iterations like Nesterov's method [Med. Phys. 42, 2699 (2015)].

The use of only a portion of the projections (i.e. where the subset is smaller than the full set) can speed up computation in various ways. For example, the data sets are smaller and thus may be stored in local memory, and thus not have to be swapped in and out of local memory. Further, the reconstructed volume can be updated more often, since each subiteration is based on less data. In this manner, the reconstructed volume is updated more frequently and improves more quickly.

For example, there can be 600 images measured from the CBCT scan. A subset may include 100 images, and a first subiteration can be performed to obtain a reconstructed volume. Then, the next 100 images can start with the new reconstructed volume and update that volume using the next 100 images. The process can continue with further subsets until all of the images have been used. Then, the reconstructed volume obtained after the final subset can be used in a next subiteration for the first subset of 100 images.

In some embodiments, to allow for on-line applications, the computational demand can be taken into account by massive parallelization and respective hardware. Suited for this purpose are systems with one or multiple GPU cards.

VII. Use of Prior Knowledge

Another advantage of embodiments compared to the FBP is that prior knowledge can be included in the reconstruction process. There are different types of knowledge that can be included, e.g. physical models, object models, and statistical models.

A. Physical Models

Physical models can directly be integrated into forward and backward projection operators. Examples are finite focal spot size, focal spot shape, detector response, source spectrum, beam hardening, and scatter events. Alternatively, such properties can be taken into account by correction or conversion steps during preprocessing. These properties can make simulations more realistic and bring those closer to the actual measurements.

B. Object Model (Regularization)

Embodiments can assume that the volume is piece-wise constant, which can directly result in image noise suppression. Such a process is called regularization herein. This regularization can be integrated into the reconstruction process by adding a regularization term to the cost function, e.g., in addition to a data fidelity term that corresponds to a size of residual volume 640 (i.e., the size of the error).

The regularization term can act as a penalty for having large differences from one voxel to a neighboring voxel. In one embodiment, the total variation is used as the regularization term. The total variation can correspond to the norm of the gradient, and typically the L1 norm (sum of absolute differences). Thus, the regularization term is a constraint for the optimization of the reconstructed volume, so that the final reconstructed volume does not have too much noise. In this manner, the update to the reconstructed volume can be in a direction of a smoother reconstructed volume.

Another technique can be to apply a smoothing function to the reconstructed volume and/or the residual volume. The smoothing function could be an average of the voxel values in the neighborhood of the voxel, e.g., within a spherical shell of a predetermined radius. The smoothing function can include edge-preserving properties like the bilateral filter.

Figure 9A:
FIG. 9A shows a reconstructed image of True Beam dataset used for FIGS. 5B and 5C applying iterative reconstruction techniques without regularization according to embodiments of the present invention.
Figure 9B:
FIG. 9B shows a reconstructed image of True Beam dataset used for FIGS. 5B and 5C applying iterative reconstruction techniques with total variation (TV) regularization according to embodiments of the present invention.

FIG. 9A shows a reconstructed image 910 of True Beam dataset from FIG. 5C applying iterative reconstruction techniques without regularization according to embodiments of the present invention. FIG. 9B shows a reconstructed image 950 of True Beam dataset from FIG. 5C applying iterative reconstruction techniques with total variation (TV) regularization according to embodiments of the present invention.

C. Statistical Models

To account for quantum noise statistics, a statistical weighting model can be used, e.g., to be used as part of operator 645. Quantum noise is Poisson distributed, which means that signal intensity increases with the number of measured photons, but signal-to-noise ratio increases too. Thus, the optimization would favor the agreement with measured values of high counts (low attenuation along line integral) over low counts (high attenuation along line integral). Two different ways to realize this are provided below.

One is to explicitly add a weight depending on the detector pixel counts resulting in a penalized weighted least square (PWLS) approach. Because the signal-to-noise ratio increases with increasing counts, the higher the number of counts for a voxel, the higher the weighting is. Another option is to account for this implicitly within a statistical reconstruction approach as has been done within implementations below. Here, the log-likelihood optimization automatically results in a weight that depends on the pixel counts and that can be included in a normalization step.

The statistical weights can effectively be stored as another volume that is multiplied against one or more residual volume that are used to update the reconstructed volume. In one embodiment, the statistical weights can be applied within node 630 of FIG. 6. Each voxel value of the statistical volume carries information about how much each voxel is to be updated based on noise suppression. The statistical weight corresponds to measured intensities within detector pixels. If the attenuation along a ray is high (i.e. associated pixels intensities at the image detector are low), embodiments can presume a bigger influence from noise. That is, the measurement with low signals is more affected by noise. Thus, embodiments can emphasize pixels that experience less attenuation, and these pixels are associated with less noise and more reliable data. When the statistical weights are applied as volume weights, e.g., at operator 645, voxels associated with noisy pixels have smaller weights, and voxels associated with less noise would have higher rates. In other embodiments, the statistical weights can be applied at node 630.

Nevertheless which option is chosen, the result is a noise suppression behavior. An example is IGRT in abdominal or pelvic region where image quality is usually deteriorated by streak artefacts. Due to correlated noise and options from diagnostic CT like tube current, modulation are generally not possible due to the large cone angle. There is an additional advantage of this statistical weight when metal objects are present. Metal objects do have a very high attenuation and thus the remaining primary signal of a ray through metal is usually very small compared to scatter and noise. Those rays also receive a low weight and thus the impact of photon starvation, scatter, and noise can be implicitly reduced.

Figure 10B:
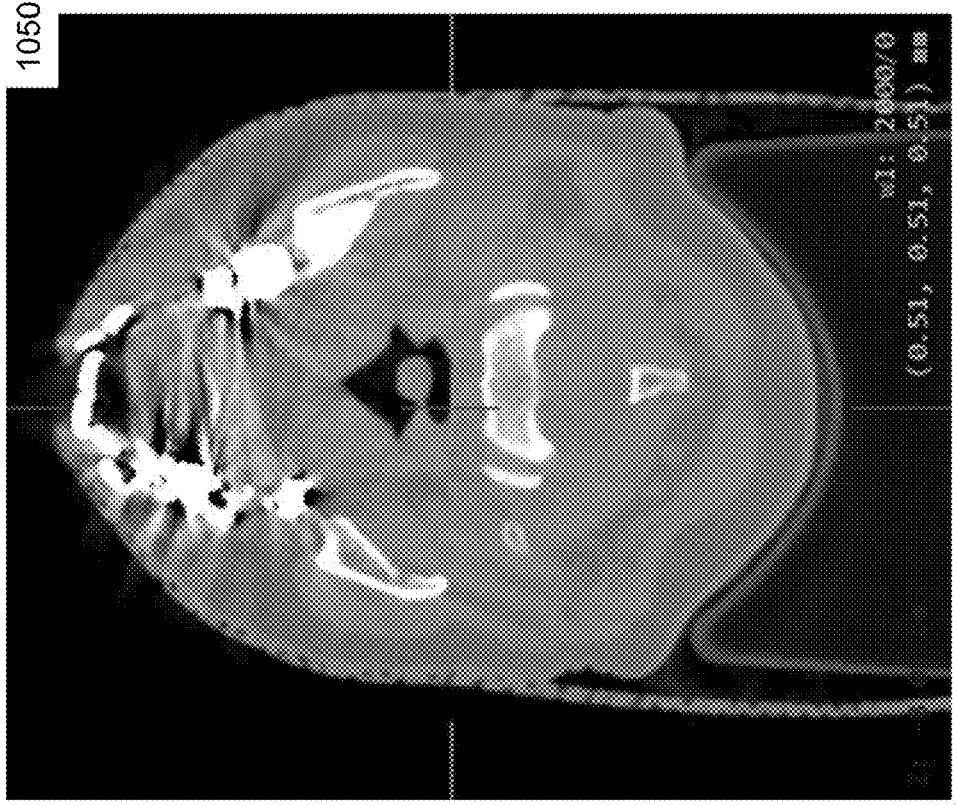
FIG. 10B shows a reconstructed image 1050 with a statistical reconstruction algorithm for a patient with dental implants according to embodiments of the present invention.
Figure 10A:
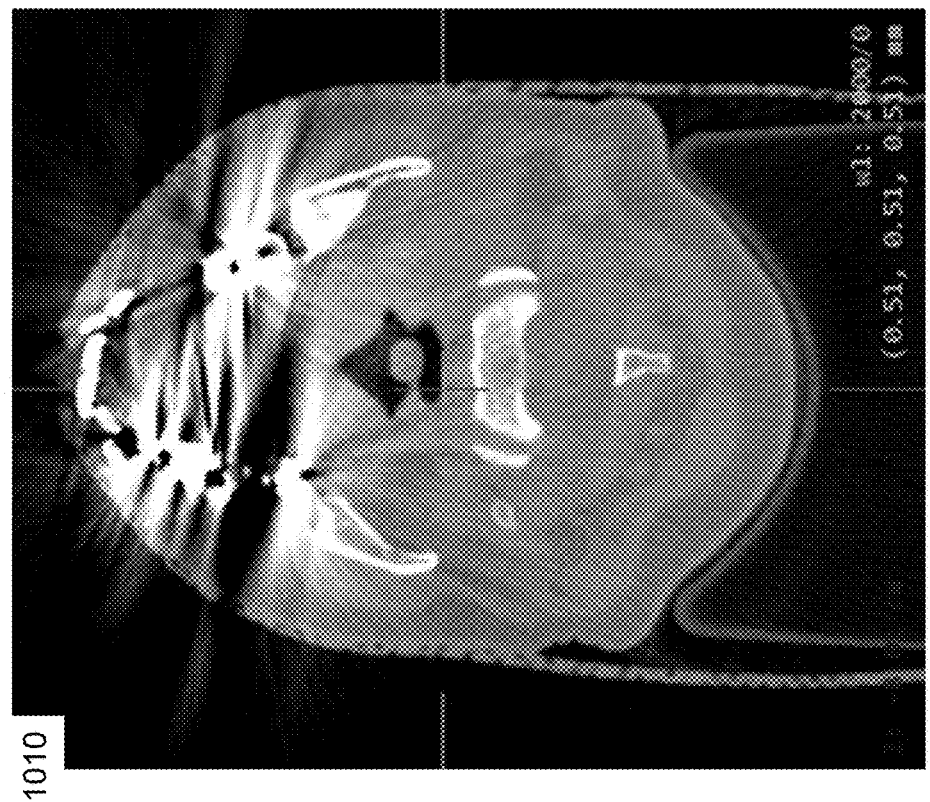
FIG. 10A shows a daily CBCT image 1010 on a True Beam machine for a patient with dental implants.

FIG. 10A shows a daily CBCT image 1010 on a True Beam machine for a patient with dental implants. This is a reconstructed CBCT image using FBP. FIG. 10B shows a reconstructed image 1050 with a statistical IR algorithm for a patient with dental implants according to embodiments of the present invention. FIG. 10B shows improvements in the presence of metal.

VIII. Motion

An inherent problem in CBCT reconstruction is the occurrence of patient motion and subsequent artifacts due to the longer acquisition time compared to diagnostic CT systems. For example, the acquisition of the CBCT takes around 1 minute, and the patient can move within the acquisition time. Therefore, there are artifacts because the projections are not consistent over the full scan time.

Some embodiments can address this specific problem by reducing the impact of inconsistencies (due to motion) in the measured projection data by down weighting certain data (e.g., certain rays). This reduction can be achieved implicitly by outlier robust data fidelity definitions or explicitly by detecting the affected data and down-weighting that data. In one implementation, local deformations can be estimated to compensate for the motion.

Figure 11:
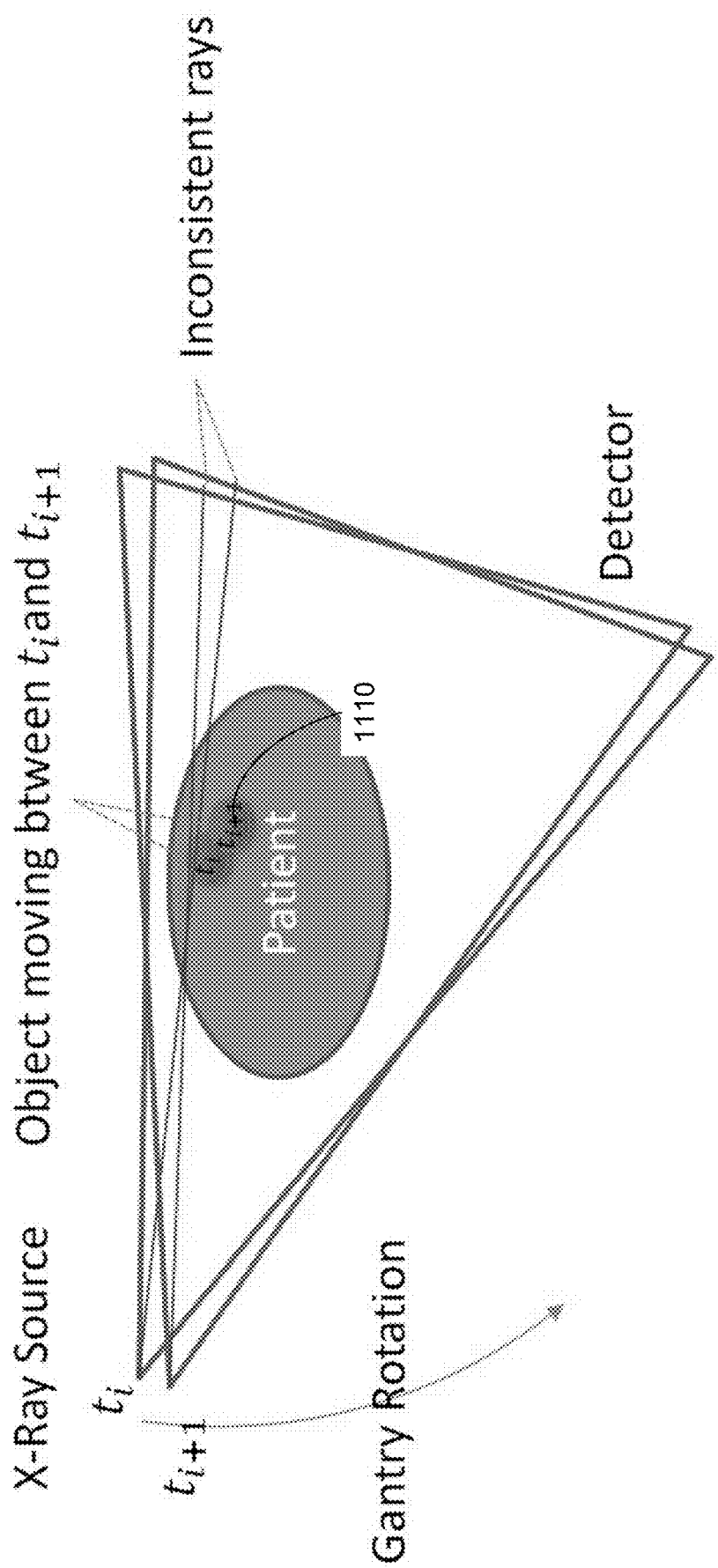
FIG. 11 shows a schematic illustration of how moving objects (e.g. organs) cause data inconsistencies in measured projection data.

FIG. 11 shows a schematic illustration of how moving objects (e.g. organs) cause data inconsistencies in measured projection data. A patient is shown with an object 1110, e.g., a tumor, which is to be irradiated. Two positions of the radiation source are shown at two time points, $t_i$ and $t_{i+1}$ as part of obtaining the plurality of projection images for the plurality of geometries. Ideally, object 1110 does not move between the two time points, as then the projection images reflect a same volume. But, with the motion of object 1110, artifacts arise. For example, certain pixels will have a different value for the projection image at $t_{i+1}$ relative to what it would be if object 1110 had not moved.

Embodiments can identify such pixels that are effected by motion. These pixels can be down-weighted in the reconstruction (e.g., to zero or to some lower value). Thus, these pixels that are associated with noise do not affect the volume reconstruction as much, and the introduced noise due to motion is reduced.

In some embodiments, weights can be applied on the residual images before/during back projection. Criteria can be used to separate between good and bad pixel conditions, e.g., inconsistent changes in values from one image to another. Bad pixels can be down-weighted in the residual images. In other embodiments, as described above, functions like Huber-loss can be used within data fidelity function to provide a weighting of the projection data. The weight can implicitly include the separation between good and bad pixel conditions.

IX. Post-Processing

Image noise can be already addressed by regularization part and by statistical weighting. Nevertheless, there are potentially reasons to apply post-processing procedures in addition right after the iteration process is finished. Examples are edge-preserving smoothing filters like the bilateral filter. The balance between data fidelity and regularization can be chosen carefully for convergence reasons issues and thus further noise reduction might be desirable.

X. Computer System

Figure 12:
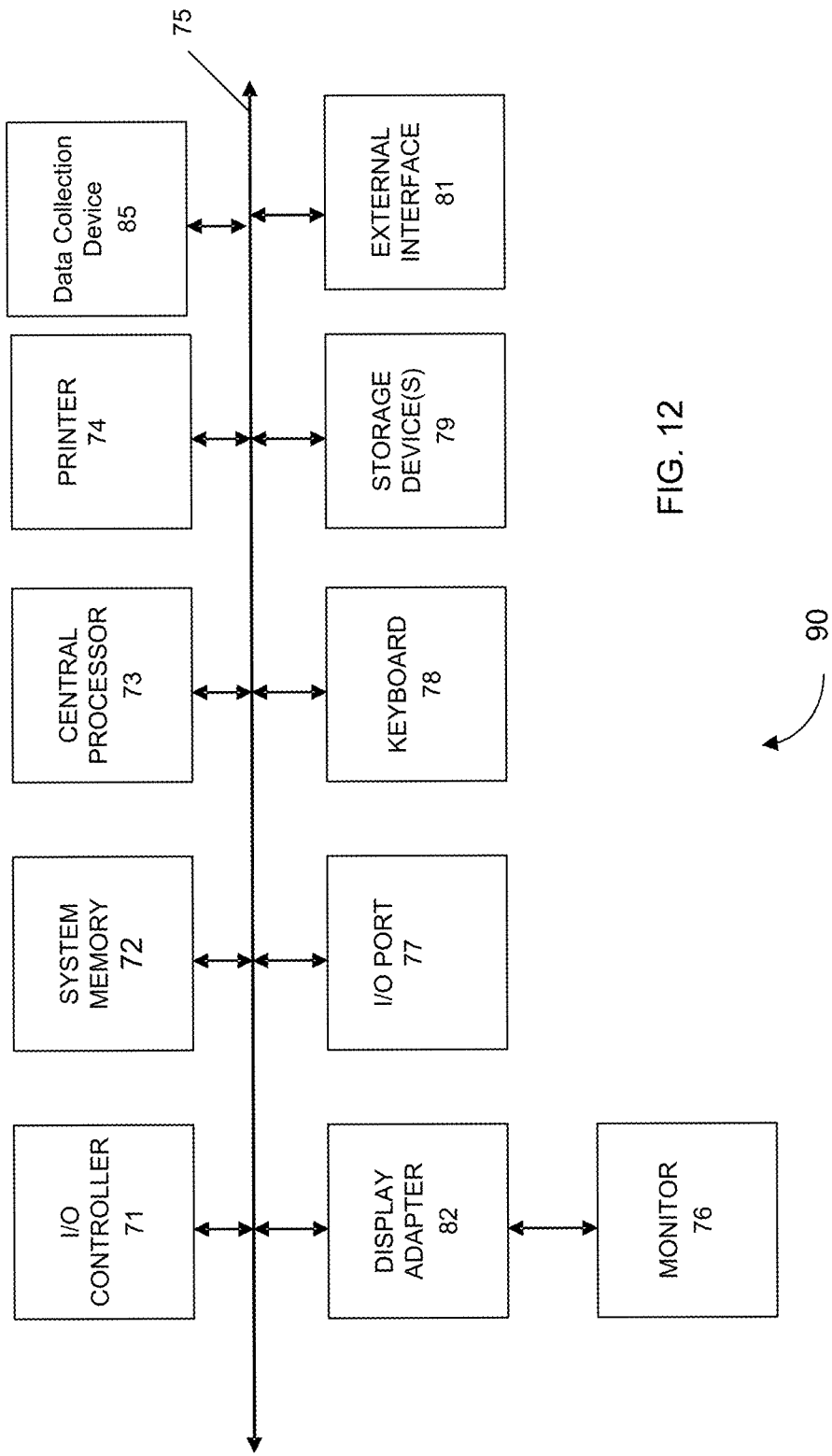
FIG. 12 shows a block diagram of an example computer system usable with system and methods according to embodiments of the present invention.

Any of the computer systems mentioned herein may utilize any suitable number of subsystems. Examples of such subsystems are shown in FIG. 12 in computer system 90. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 12 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 90 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method of imaging a patient, the method comprising:
   perform a cone-beam computed tomography (CBCT) scan of a region of the patient using a radiation source to obtain a plurality of projection images, each projection image being taken at a different one of a plurality of geometries of the radiation source relative to the patient, wherein the region of the patient includes a tumor;
   determining, by a computer system, a reconstructed volume of the patient by performing one or more iterations, each iteration comprising:
   receiving a starting reconstructed volume for the region, the starting reconstructed volume comprising a three-dimensional grid of voxels;
   for each of a subset of the plurality of geometries:
   simulating rays from the radiation source through the starting reconstructed volume to a virtual two-dimensional detector to obtain a subset of virtual images;
   comparing the subset of virtual images to a corresponding subset of the plurality of projection images to determine a subset of residual images, each residual image comprising an array of residual pixels, wherein determining the subset of residual images includes:
   comparing measured pixels between different projection images in the corresponding subset of the projection images to identify inconsistent pixels; and
   down-weighting the residual pixels corresponding to the inconsistent pixels;
   constructing a residual volume comprising a three-dimensional grid of residual voxels based on the subset of residual images;
   combining the residual volume and the starting reconstructed volume to obtain a new reconstructed volume; and
   determining whether the new reconstructed volume satisfies one or more stopping criteria or whether another iteration is to be performed.

2. The method of claim 1, wherein constructing the residual volume includes:
   for each of the residual pixels of each of the residual images:
   determining a set of residual voxels that intersect with rays from the residual pixel to the radiation source;
   for each of the residual voxels in the set of residual voxels, determining a contribution to the residual voxel; and
   for each of the residual voxels in the set of residual voxels:
   accumulating the contributions for the residual voxel to obtain the residual volume.

3. The method of claim 1, wherein obtaining the new reconstructed volume further includes:
   determining a penalty volume that represents a variation of voxels of the starting reconstructed volume; and
   combining the penalty volume, starting reconstructed volume, and the residual volume to obtain the new reconstructed volume.

4. The method of claim 1, further comprising:
   applying a smoothing function to the residual voxels of the residual volume and/or to the new reconstructed volume.

5. The method of claim 1, wherein combining the residual volume and the starting reconstructed volume to obtain the new reconstructed volume includes:
   applying a respective weighting factor to each residual voxel of the residual volume, wherein the weighting factor for a residual voxel is determined based on a level of attenuation corresponding to the projection images.

6. The method of claim 1, wherein combining the residual volume and the starting reconstructed volume to obtain the new reconstructed volume includes:
storing one or more previous residual volumes from one or more previous iterations;
using the one or more previous residual volumes in determining the new reconstructed volume.

7. The method of claim 1, further comprising:
aligning, by the computer system, the reconstructed volume to a treatment planning volume to identify one or more changes associated with the tumor, wherein a current radiation treatment plan had been determined using the treatment planning volume;
updating a characteristic of a radiation treatment procedure based on the one or more changes to obtain an updated radiation treatment procedure; and
providing a radiation treatment to the patient using the updated radiation treatment procedure.

8. The method of claim 7, wherein the updated characteristic is a position of the patient.

9. The method of claim 7, wherein the updated characteristic is a dosage of radiation to be applied in the radiation treatment procedure.

10. The method of claim 7, further comprising:
segmenting, by the computer system, the reconstructed volume to identify a segment corresponding the tumor, wherein the alignment uses the segment corresponding the tumor.

11. A system comprising:
an imaging device for performing cone-beam computed tomography (CBCT) scans, the imaging device including a radiation source and an imaging detector configured to perform a CBCT scan of a region of a patient using the radiation source to obtain a plurality of projection images, each projection image being taken at a different one of a plurality of geometries of the radiation source relative to the patient, wherein the region of the patient includes a tumor;
one or more processors of a computer system configured to:
determine a reconstructed volume of the patient by performing one or more iterations, each iteration comprising:
receiving a starting reconstructed volume for the region, the starting reconstructed volume comprising a three-dimensional grid of voxels;
for each of a subset of the plurality of geometries:
simulating rays from the radiation source through the starting reconstructed volume to a virtual two-dimensional detector to obtain a subset of virtual images;
comparing the subset of virtual images to a corresponding subset of the plurality of projection images to determine a subset of residual images, each residual image comprising an array of residual pixels;
constructing a residual volume comprising a three-dimensional grid of residual voxels based on the subset of residual images, wherein determining the subset of residual images includes:
comparing measured pixels between different projection images in the corresponding subset of the projection images to identify inconsistent pixels; and
down-weighting the residual pixels corresponding to the inconsistent pixels;
combining the residual volume and the starting reconstructed volume to obtain a new reconstructed volume; and
determining whether the new reconstructed volume satisfies one or more stopping criteria or whether another iteration is to be performed.

12. The system of claim 11, wherein obtaining the new reconstructed volume further includes:
determining a penalty volume that represents a variation of voxels of the starting reconstructed volume; and
combining the penalty volume, starting reconstructed volume, and the residual volume to obtain the new reconstructed volume.

13. The system of claim 11, wherein combining the residual volume and the starting reconstructed volume to obtain the new reconstructed volume includes:
applying a respective weighting factor to each residual voxel of the residual volume, wherein the weighting factor for a residual voxel is determined based on a level of attenuation corresponding to the projection images.

14. The system of claim 11, wherein combining the residual volume and the starting reconstructed volume to obtain the new reconstructed volume includes:
storing one or more previous residual volumes from one or more previous iterations;
using the one or more previous residual volumes in determining the new reconstructed volume.

15. The system of claim 11, wherein the one or more processors of the computer system are further configured to:
align the reconstructed volume to a treatment planning volume to identify one or more changes associated with the tumor, wherein a current radiation treatment plan had been determined using the treatment planning volume; and
determine an updated characteristic of a radiation treatment procedure based on the one or more changes to obtain an updated radiation treatment procedure,
the system further comprising:
a radiation source for providing radiation to the tumor based on the updated radiation treatment procedure.

* * * * *